(12) United States Patent
Shelton, IV et al.

(10) Patent No.: US 12,089,842 B2
(45) Date of Patent: Sep. 17, 2024

(54) FIRING BAILOUT SYSTEM FOR POWERED SURGICAL STAPLER

(71) Applicant: Cilag GmbH International, Zug (CH)

(72) Inventors: Frederick E. Shelton, IV, Hillsboro, OH (US); Kevin M. Fiebig, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 320 days.

(21) Appl. No.: 17/402,749

(22) Filed: Aug. 16, 2021

(65) Prior Publication Data

US 2023/0045998 A1 Feb. 16, 2023

(51) Int. Cl.
| | |
|---|---|
| A61B 17/072 | (2006.01) |
| A61B 17/068 | (2006.01) |
| A61B 34/00 | (2016.01) |
| A61B 34/30 | (2016.01) |

(52) U.S. Cl.
CPC ........ *A61B 17/072* (2013.01); *A61B 17/0686* (2013.01); *A61B 34/30* (2016.02); *A61B 34/71* (2016.02); *A61B 2017/07257* (2013.01); *A61B 2017/07271* (2013.01); *A61B 2017/07278* (2013.01); *A61B 2034/715* (2016.02)

(58) Field of Classification Search
CPC ............. A61B 17/072; A61B 17/0686; A61B 2017/07257; A61B 2017/07271; A61B 2017/07278
See application file for complete search history.

(56) References Cited

U.S. PATENT DOCUMENTS

| | | | |
|---|---|---|---|
| 5,129,570 | A | 7/1992 | Schulze et al. |
| 7,404,508 | B2 | 7/2008 | Smith et al. |
| 7,434,715 | B2 | 10/2008 | Shelton, IV et al. |
| 7,721,930 | B2 | 5/2010 | McKenna et al. |

(Continued)

FOREIGN PATENT DOCUMENTS

| | | |
|---|---|---|
| EP | 3437582 A1 | 2/2019 |
| WO | WO 2015/153642 A1 | 10/2015 |

(Continued)

OTHER PUBLICATIONS

U.S. Appl. No. 17/402,679.

(Continued)

*Primary Examiner* — Michelle Lopez
(74) *Attorney, Agent, or Firm* — Frost Brown Todd LLP

(57) ABSTRACT

A surgical instrument includes a body, a shaft assembly, an end effector, an actuation assembly, and a bailout mechanism. The shaft assembly extends distally from the body. The end effector is disposed on a distal end of the shaft assembly and includes a first jaw and a second jaw. The actuation assembly includes a pusher member configured to move relative to the end effector to drive movement of the first jaw, the second jaw, or both the first jaw and the second jaw. The bailout mechanism includes a first elongate actuation element and a second elongate actuation element. A portion of the bailout mechanism is configured to selectively apply tension to the first elongate actuation element and the second elongate actuation element to move the pusher member. The first elongate actuation element is stronger in tension than the second elongate actuation element cable.

20 Claims, 17 Drawing Sheets

(56) References Cited

U.S. PATENT DOCUMENTS

| | | | |
|---|---|---|---|
| 7,810,692 | B2 | 10/2010 | Hall et al. |
| 7,832,408 | B2 | 11/2010 | Shelton, IV et al. |
| 7,845,537 | B2 | 12/2010 | Shelton, IV et al. |
| 8,083,120 | B2 | 12/2011 | Shelton, IV et al. |
| 8,210,411 | B2 | 7/2012 | Yates et al. |
| 8,408,439 | B2 | 4/2013 | Huang et al. |
| 8,453,914 | B2 | 6/2013 | Laurent et al. |
| 8,708,213 | B2 | 4/2014 | Shelton, IV et al. |
| 9,060,770 | B2 | 6/2015 | Shelton, IV et al. |
| 9,186,142 | B2 | 11/2015 | Fanelli et al. |
| 9,517,065 | B2 | 12/2016 | Simms et al. |
| 9,622,746 | B2 | 4/2017 | Simms et al. |
| 9,717,497 | B2 | 8/2017 | Zerkle et al. |
| 9,795,379 | B2 | 10/2017 | Leimbach et al. |
| 9,808,248 | B2 | 11/2017 | Hoffman |
| 9,839,487 | B2 | 12/2017 | Dachs, II |
| 10,011,018 | B2 | 7/2018 | McGrogan et al. |
| 10,092,292 | B2 | 10/2018 | Boudreaux et al. |
| 10,307,170 | B2 | 6/2019 | Parfett et al. |
| 10,485,621 | B2 | 11/2019 | Morrissette et al. |
| 10,537,400 | B2 | 1/2020 | Dachs, II et al. |
| 10,610,313 | B2 | 4/2020 | Bailey et al. |
| 10,667,809 | B2 | 6/2020 | Bakos et al. |
| 10,806,530 | B2 | 10/2020 | Liao et al. |
| 10,863,988 | B2 | 12/2020 | Patel et al. |
| 11,020,138 | B2 | 6/2021 | Ragosta |
| 11,026,755 | B2 | 6/2021 | Weir et al. |
| 11,076,926 | B2 | 8/2021 | Ragosta et al. |
| 11,147,552 | B2 | 10/2021 | Burbank et al. |
| 11,166,773 | B2 | 11/2021 | Ragosta et al. |
| 11,234,700 | B2 | 2/2022 | Ragosta et al. |
| 11,259,884 | B2 | 3/2022 | Burbank |
| 11,779,332 | B2 | 10/2023 | Shelton, IV et al. |
| 2006/0185682 | A1 | 8/2006 | Marczyk |
| 2012/0209314 | A1 | 8/2012 | Weir et al. |
| 2015/0297228 | A1 | 10/2015 | Huitema et al. |
| 2016/0361126 | A1 | 12/2016 | Schena et al. |
| 2017/0020617 | A1 | 1/2017 | Weir et al. |
| 2017/0265865 | A1 | 9/2017 | Burbank |
| 2017/0265954 | A1 | 9/2017 | Burbank et al. |
| 2017/0319200 | A1* | 11/2017 | Nicholas ............... A61B 34/71 |
| 2017/0333037 | A1 | 11/2017 | Wellman et al. |
| 2018/0049835 | A1 | 2/2018 | Shelton, IV et al. |
| 2018/0051780 | A1 | 2/2018 | Shelton, IV et al. |
| 2018/0168756 | A1 | 6/2018 | Liao et al. |
| 2018/0271608 | A1 | 9/2018 | Ragosta et al. |
| 2018/0310935 | A1 | 11/2018 | Wixey |
| 2018/0325606 | A1 | 11/2018 | Weir et al. |
| 2018/0344419 | A1 | 12/2018 | Dachs, II et al. |
| 2019/0038371 | A1 | 2/2019 | Wixey et al. |
| 2019/0076142 | A1 | 3/2019 | Wixey |
| 2019/0076143 | A1 | 3/2019 | Smith |
| 2019/0167266 | A1 | 6/2019 | Patel et al. |
| 2019/0200989 | A1 | 7/2019 | Burbank et al. |
| 2019/0239967 | A1 | 8/2019 | Ragosta et al. |
| 2019/0262088 | A1 | 8/2019 | Burbank |
| 2020/0138529 | A1 | 5/2020 | Ragosta et al. |
| 2020/0397430 | A1 | 12/2020 | Patel et al. |
| 2020/0405301 | A1 | 12/2020 | Shelton, IV et al. |
| 2021/0393340 | A1 | 12/2021 | Beckman et al. |
| 2021/0401433 | A1 | 12/2021 | Freidel et al. |

FOREIGN PATENT DOCUMENTS

| | | | |
|---|---|---|---|
| WO | WO 2017/083125 | A1 | 5/2017 |
| WO | WO 2017/083129 | A1 | 5/2017 |
| WO | WO 2018/049198 | A1 | 3/2018 |
| WO | WO 2018/049206 | A1 | 3/2018 |
| WO | WO 2018/049211 | A1 | 3/2018 |
| WO | WO 2018/049217 | A1 | 3/2018 |
| WO | WO 2018/052806 | A1 | 3/2018 |
| WO | WO 2018/052810 | A1 | 3/2018 |
| WO | WO 2018/071497 | A1 | 4/2018 |
| WO | WO 2018/071763 | A1 | 4/2018 |
| WO | WO 2018/085529 | A2 | 5/2018 |
| WO | WO 2018/175467 | A1 | 9/2018 |
| WO | WO 2019/165403 | A1 | 8/2019 |
| WO | WO 2020/131290 | A1 | 6/2020 |

OTHER PUBLICATIONS

U.S. Appl. No. 17/088,941, entitled "Surgical Stapler End Effector Sled Having Cartridge Wall Support Feature," filed Nov. 4, 2020.
U.S. Appl. No. 17/402,674, entitled "Methods of Operating a Robotic Surgical Stapler," filed Aug. 16, 2021.
U.S. Appl. No. 17/402,675, entitled "Multi-Threshold Motor Control Algorithm for Powered Surgical Stapler," filed Aug. 16, 2021.
U.S. Appl. No. 17/402,677, entitled "Variable Response Motor Control Algorithm for Powered Surgical Stapler," filed Aug. 16, 2021.
U.S. Appl. No. 17/402,679, entitled "Powered Surgical Stapler Having Independently Operable Closure and Firing Systems," filed Aug. 16, 2021.
U.S. Appl. No. 17/402,695, entitled "Firing System Features for Surgical Stapler," filed Aug. 16, 2021.
U.S. Appl. No. 17/402,701, entitled "Multiple-Sensor Firing Lockout Mechanism for Powered Surgical Stapler," filed Aug. 16, 2021.
U.S. Appl. No. 17/402,703, entitled "Proximally Located Firing Lockout Mechanism for Surgical Stapler," filed Aug. 16, 2021.
U.S. Appl. No. 17/402,720, entitled "Cartridge-Based Firing Lockout Mechanism for Surgical Stapler," filed Aug. 16, 2021.
U.S. Appl. No. 17/402,732, entitled "Multi-Position Restraining Member for Sled Movement," filed Aug. 16, 2021.
U.S. Appl. No. 17/402,738, entitled "Firing Member Tracking Feature for Surgical Stapler," filed Aug. 16, 2021.
U.S. Appl. No. 17/402,744, entitled "Adjustable Power Transmission Mechanism for Powered Surgical Stapler," filed Aug. 16, 2021.
U.S. Appl. No. 17/402,759, entitled "Deflectable Firing Member for Surgical Stapler," filed Aug. 16, 2021.
U.S. Appl. No. 17/402,674.
U.S. Appl. No. 17/402,675.
U.S. Appl. No. 17/402,677.
U.S. Appl. No. 17/402,695.
U.S. Appl. No. 17/402,701.
U.S. Appl. No. 17/402,703.
U.S. Appl. No. 17/402,720.
U.S. Appl. No. 17/402,732.
U.S. Appl. No. 17/402,738.
U.S. Appl. No. 17/402,744.
U.S. Appl. No. 17/402,759.
International Search Report and Written Opinion dated Feb. 17, 2023 for Application No. PCT/IB2022/057613, 18 pgs.

* cited by examiner

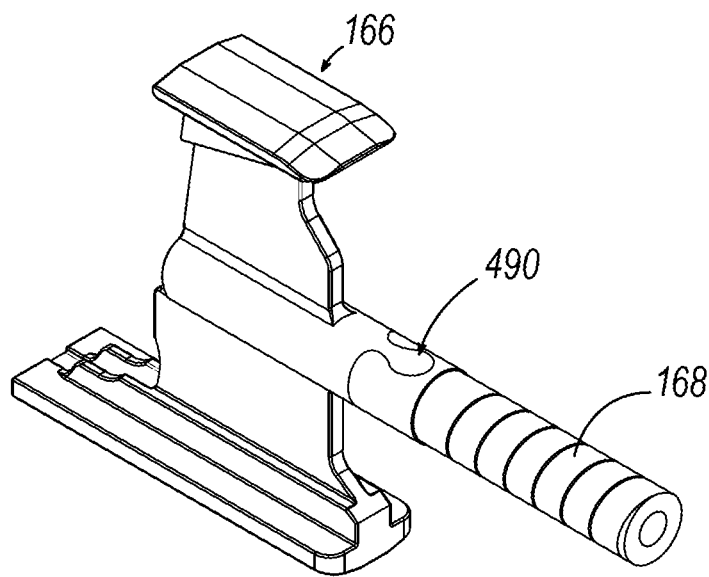
FIG. 18
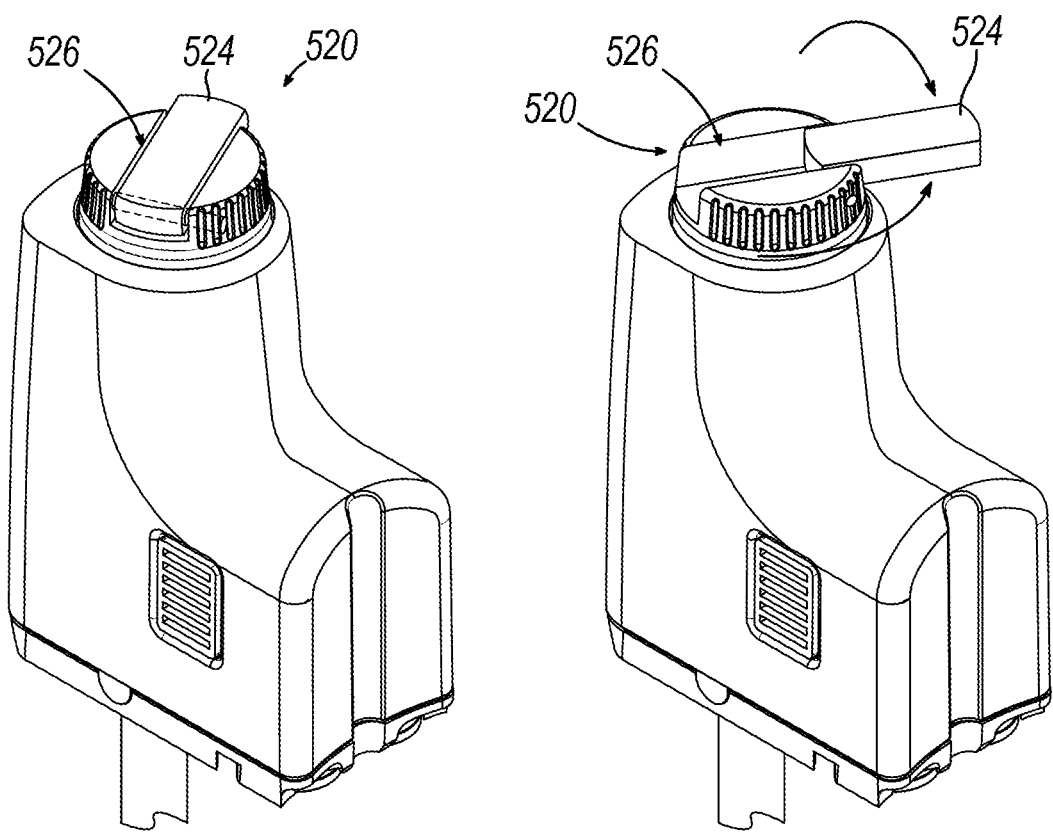
FIG. 19A  FIG. 19A

FIRING BAILOUT SYSTEM FOR POWERED SURGICAL STAPLER

BACKGROUND

A variety of surgical instruments include an end effector for use in conventional medical treatments and procedures conducted by a medical professional operator, as well as applications in robotically assisted surgeries. Such surgical instruments may be directly gripped and manipulated by a surgeon or incorporated into robotically surgical systems. In the case of robotically assisted surgery, the surgeon may operate a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletal gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a surgical stapler, a tissue grasper, a needle driver, an electrosurgical cautery probe, etc. Each of these structures performs functions for the surgeon, for example, cutting tissue, coagulating tissue, holding or driving a needle, grasping a blood vessel, dissecting tissue, or cauterizing tissue.

Examples of surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Examples of surgical staplers and associated features are disclosed in U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; U.S. Pat. No. 8,453,914, entitled "Motor-Driven Surgical Cutting Instrument with Electric Actuator Directional Control Assembly," issued Jun. 4, 2013; U.S. Pat. No. 9,186,142, entitled "Surgical Instrument End Effector Articulation Drive with Pinion and Opposing Racks," issued on Nov. 17, 2015; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 10,092,292, entitled "Staple Forming Features for Surgical Stapling Instrument," issued Oct. 9, 2018; U.S. Pat. No. 9,717,497, entitled "Lockout Feature for Movable Cutting Member of Surgical Instrument," issued Aug. 1, 2017; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; and U.S. Pat. No. 8,210,411, entitled "Motor-Driven Surgical Instrument," issued Jul. 3, 2012. The disclosure of each of the above-cited U.S. Patents is incorporated by reference herein in its entirety.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 18 depicts a perspective view of an axial strengthening feature that may be incorporated into the surgical instrument of FIG. 4;

FIG. 19A depicts a perspective view of a manual drive wheel that may be incorporated into the bailout mechanisms of FIG. 12 or 13, with an arm of the manual drive wheel in a retracted position;

FIG. 19B depicts another perspective view of the manual drive wheel of FIG. 19A, with the arm of the manual drive wheel in an extended position;

Figure 1:
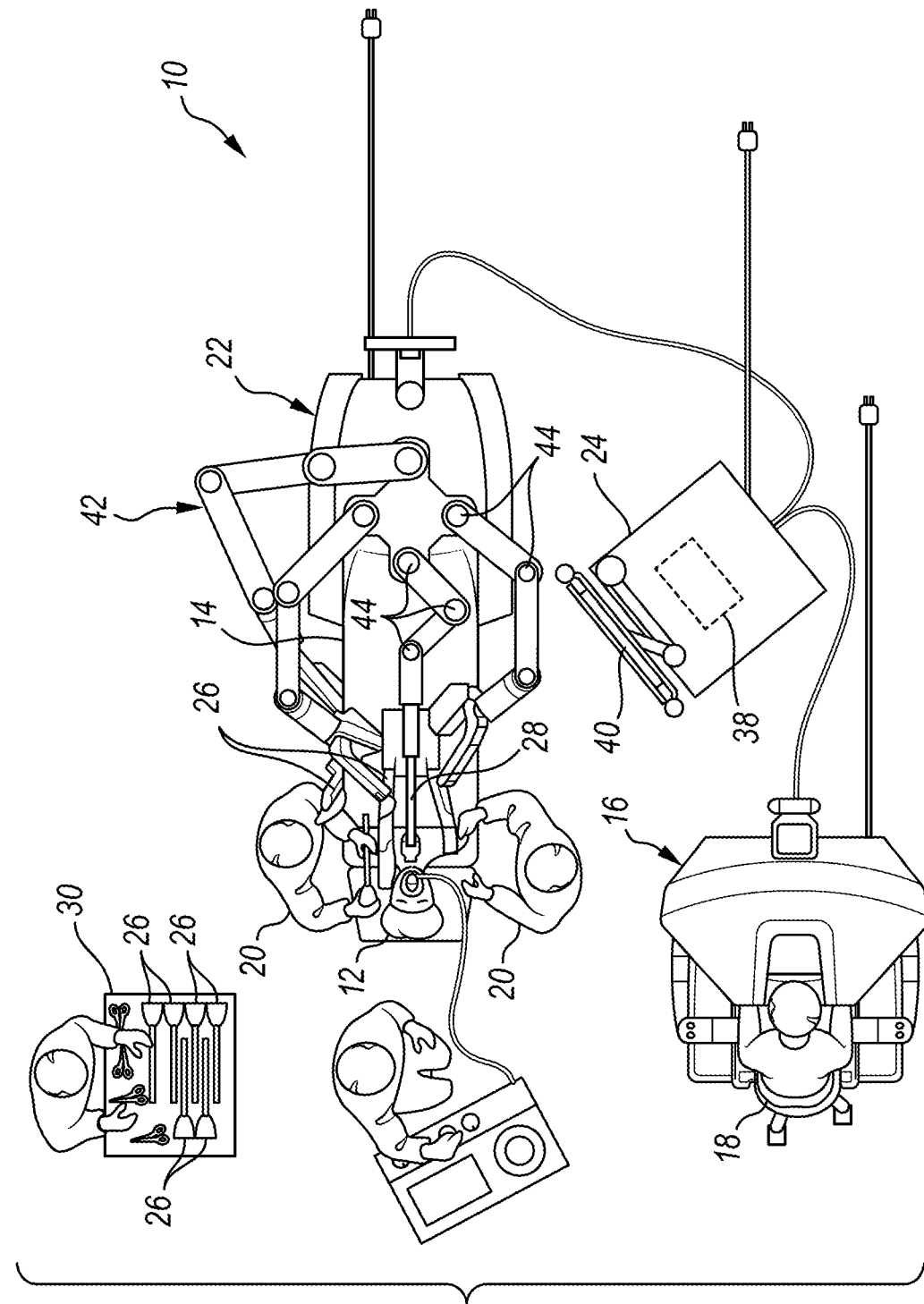
FIG. 1 depicts a top plan view of a robotic surgical system being used to perform a surgical procedure.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "clockwise," "counterclockwise," "inner," "outer," "upper," "lower," and the like also are used herein for reference to relative positions and directions. Such terms are used below with reference to views as illustrated for clarity and are not intended to limit the invention described herein.

Aspects of the present examples described herein may be integrated into a robotically-enabled medical system, including as a robotic surgical system, capable of performing a variety of medical procedures, including both minimally invasive, such as laparoscopy, and non-invasive, such as endoscopy, procedures. Among endoscopy procedures, the robotically-enabled medical system may be capable of performing bronchoscopy, ureteroscopy, gastroscopy, etc.

I. Exemplary Robotic Surgical System

A. Overview

FIG. 1 shows a top plan view of an exemplary robotic surgical system (10) that may be used for performing a diagnostic or surgical procedure on a patient (12) who is lying down on an operating table (14). Robotic surgical system (10) may be constructed and operable in accordance with at least some of the teachings of U.S. Pat. No. 9,839,487, entitled "Backup Latch Release for Surgical Instrument," issued Dec. 12, 2017; U.S. Pat. No. 10,485,621, entitled "Sterile Barrier Between Surgical Instrument and Teleoperated Actuator," issued Nov. 26, 2019; U.S. Pat. No. 10,806,530, entitled "System and Method for Patient-Side Instrument Control," issued Oct. 20, 2020; U.S. Pat. No. 10,537,400, entitled "Detection Pins to Determine Presence of Surgical Instrument and Adapter on Manipulator," issued Jan. 21, 2020; U.S. Pat. No. 10,863,988, entitled "Surgical Instrument with Lockout Mechanism," published Dec. 15, 2020; U.S. Pat. No. 10,610,313, entitled "Surgical Instrument with Shiftable Transmission," issued Apr. 7, 2020; U.S. Pub. No. 2018/0271608, entitled "Manual Release for Medical Device Drive System," published Sep. 27, 2018; U.S. Pub. No. 2018/0325606, entitled "Systems and Methods for Operating an End Effector," published Nov. 15, 2018; U.S. Pub. No. 2019/0200989, entitled "Stapler Reload Detection and Identification," published Jul. 4, 2019; U.S. Pub. No. 2019/0239967, entitled "Stapler Beam Architecture," published Aug. 8, 2019; U.S. Pub. No. 2019/0262088, entitled "Robotic Surgical Stapler Assembly Configured to Use Stapler Reload," published Aug. 29, 2019; U.S. Pub. No. 2019/0239877, entitled "Wrist Architecture," published Aug. 8, 2019; U.S. Pub. No. 2019/0201150, entitled "Push-Pull Surgical Instrument End Effector Actuation Using Flexible Tension Member," published Jul. 4, 2019; U.S. Pub. No. 2019/0282233, entitled "Stapler Cartridge With an Integral Knife," published Sep. 19, 2019; U.S. Pub. No. 2019/0262088, entitled "Robotic Surgical Stapler Assembly Configured to Use Stapler Reload," published Aug. 29, 2019; U.S. Pub. No. 2020/0138529, entitled "Locking System for Medical Device Drive System," published May 7, 2020; and/or U.S. Pub. No. 2020/0397430, entitled "Surgical Instrument With Lockout Mechanism," published Dec. 24, 2020. The disclosure of each of the above-cited U.S. Patents and U.S. Patent Publications is incorporated by reference herein in its entirety.

Robotic surgical system (10) may include a surgeon's console (16) for use by a surgeon (18) during a surgical procedure. One or more assistants (20) may also participate in the procedure. Robotic surgical system (10) may include a patient side cart (22) (i.e., a surgical robot) and an electronics cart (24). Patient side cart (22) may manipulate at least one surgical instrument (26) (also referred to as a "tool assembly" or "tool") through an incision in the body of patient (12) while surgeon (18) views the surgical site through surgeon's console (16). As will be described in greater detail below, surgical instrument(s) (26) and an imaging device (shown as an endoscope (28)) may be removably coupled with patient side cart (22). Electronics cart (24) may be used to process the images of the surgical site for subsequent display to the surgeon (18) through surgeon's console (16). Electronics cart (24) may be coupled with endoscope (28) and may include a processor (38) (shown schematically) to process captured images for subsequent display, such as to surgeon (18) on the surgeon's console (16), on a display (40) of electronics cart (24), or another suitable display located locally and/or remotely. The images may also be processed by a combination of electronics cart (24) and processor (38), which may be coupled together to process the captured images jointly, sequentially, and/or combinations thereof. Electronics cart (24) may overlay the captured images with a virtual control interface prior to displaying combined images to the surgeon (18) via surgeon's console (16).

Figure 2:
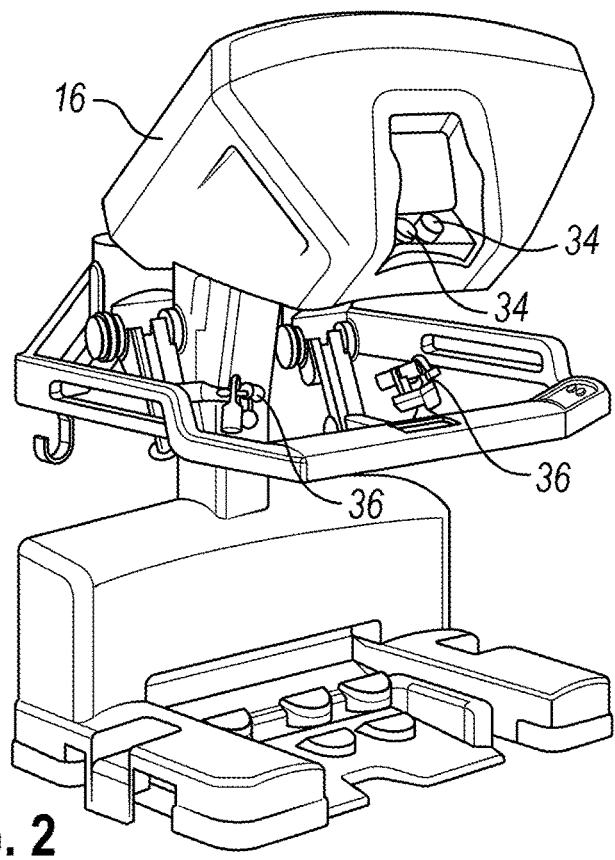
FIG. 2 depicts a perspective view of a surgeon's control console of the robotic surgical system of FIG. 1.

FIG. 2 shows a perspective view of surgeon's console (16). Surgeon's console (16) includes a left eye display (32) and a right eye display (34) for presenting surgeon (18) with a coordinated stereo view of the surgical site that enables depth perception. Surgeon's console (16) includes one or more input control devices (36) causing patient side cart (22) (shown in FIG. 1) to manipulate one or more surgical instruments (26). Input control devices (36) may provide the same degrees of freedom as their associated surgical instruments (26) (shown in FIG. 1) to provide surgeon (18) with telepresence, or the perception that the input control devices (36) are integral with surgical instruments (26). To this end, position, force, and tactile feedback sensors (not shown) may be employed to transmit position, force, and tactile sensations from surgical instruments (26) back to the surgeon's hands through input control devices (36). In some instances, surgeon's console (16) may be located in the same room as the patient so that surgeon (18) may directly monitor the procedure, be physically present if necessary, and speak to an assistant directly rather than over the telephone or other communication medium. Alternatively, surgeon (18) may be located in a different room, a completely different building, or other remote location from the patient allowing for remote surgical procedures.

Figure 3:
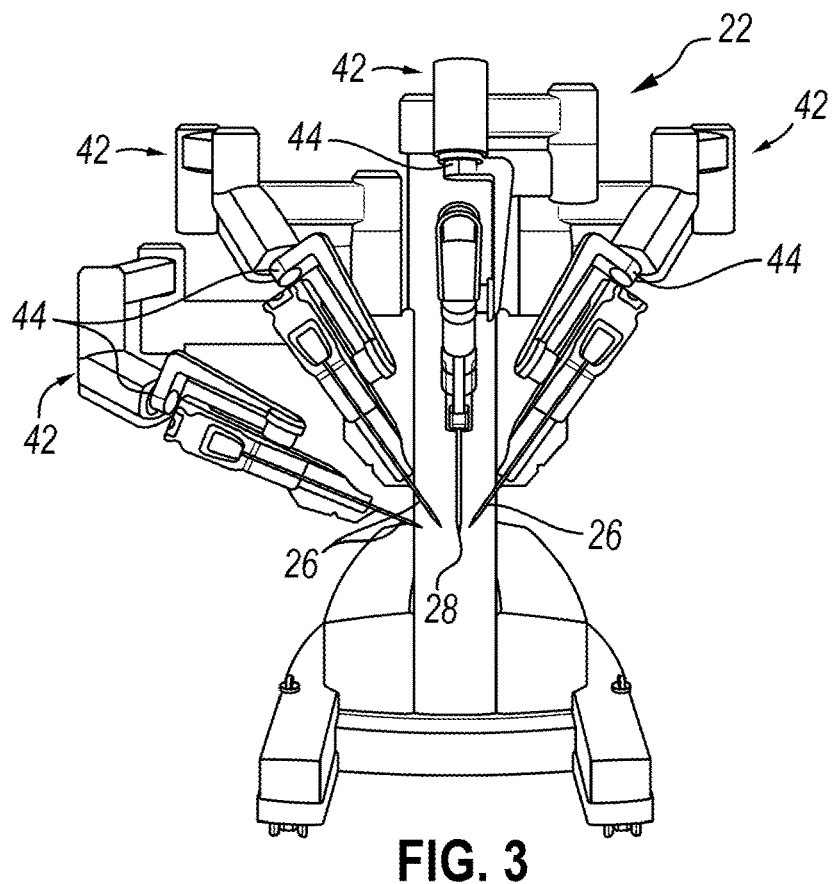
FIG. 3 depicts a front elevation view of a patient side cart of the robotic surgical system of FIG. 1.

FIG. 3 shows patient side cart (22) that manipulates surgical instruments (26). An image of the surgical site may be obtained by endoscope (28), which may include a stereoscopic endoscope. Manipulation is provided by robotic mechanisms, shown as robotic arms (42) that include at least one robotic joint (44) and an output coupler (not shown) that is configured to removable secure surgical instrument (26) with robotic arm (42). Endoscope (28) and surgical tools (26) may be positioned and manipulated through incisions in the patient so that a kinematic remote center is maintained at the incision to minimize the size of the incision. Images of the surgical site may include images of the distal ends of the surgical instruments (26) when they are positioned within the field-of-view of the endoscope (28). Patient side cart (22) may output the captured images for processing outside electronics cart (24). The number of surgical instruments (26) used at one time will generally depend on the diagnostic or surgical procedure and the space constraints within the operating room, among other factors. To change one or more of surgical instruments (26) being used during a procedure, assistant(s) (20) may remove surgical instrument (26) from patient side cart (22) and replace surgical instrument (26) with another surgical instrument (26) from a tray (30) (shown in FIG. 1) in the operating room.

B. Exemplary Surgical Instrument

Figure 4:
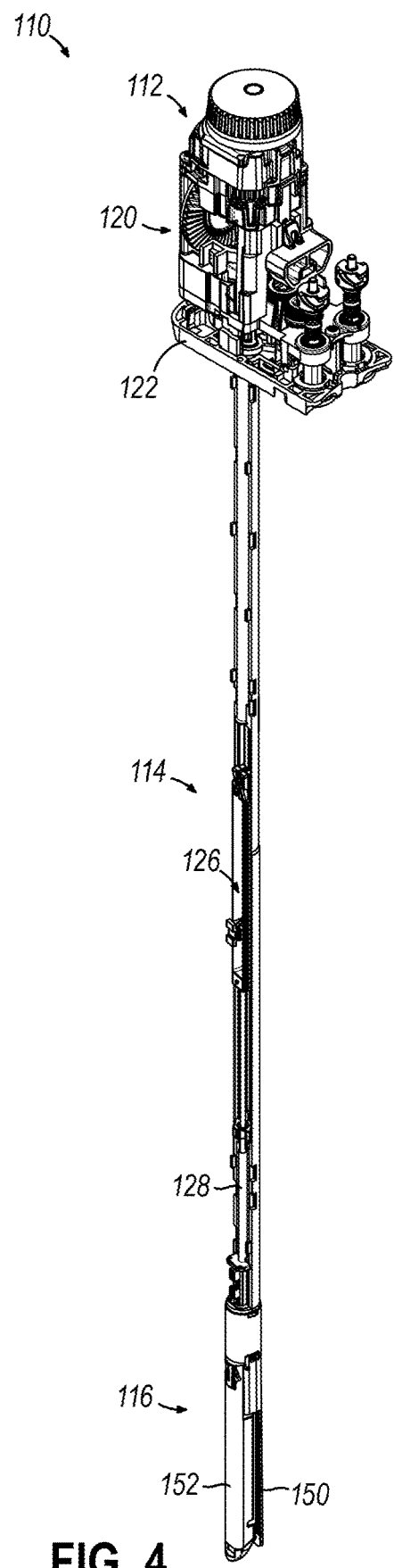
FIG. 4 depicts a perspective view of an exemplary surgical instrument that may be used with the robotic surgical system of FIG. 1, where the surgical instrument includes an instrument base, an elongate shaft, and an end effector, with select portions of the surgical instrument omitted to reveal internal features.
Figure 5:
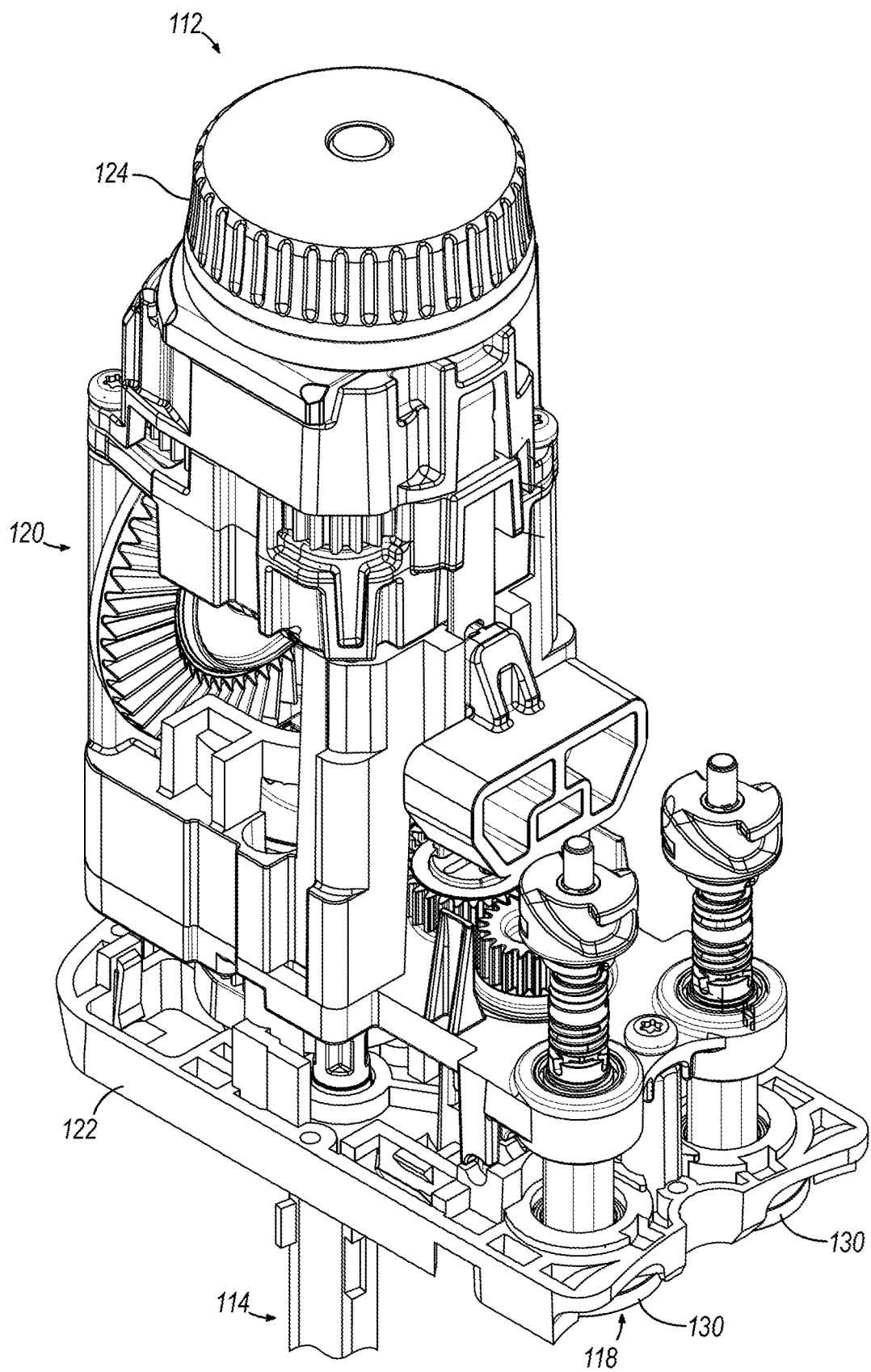
FIG. 5 depicts an enlarged perspective view of the instrument base of the surgical instrument of FIG. 4, with an outer housing omitted to reveal internal features.

FIGS. 4-5 show an exemplary surgical instrument (110) that may be mounted on and used with patient side cart (22) shown in FIG. 3. Surgical instrument (110) can have any of a variety of configurations capable of performing one or more surgical functions. As shown, surgical instrument (110) includes an instrument base (112), a shaft assembly (114) extending distally from instrument base (112), and an end effector (116) at a distal end of shaft assembly (114). Instrument base (112) includes an attachment interface (118) that includes input couplers (130) that are configured to interface with and be driven by corresponding output couplers (not shown) of robotic arm (42) of patient side cart (22).

FIG. 5 shows an enlarged perspective view of instrument base (112) of surgical instrument (110). Instrument base (112) includes a drive system (120) mounted on a chassis (122) and having one or more actuators for actuating end effector (116) to clamp, staple, and cut tissue, and for articulating end effector (116) relative to a longitudinal axis defined by shaft assembly (114). Drive system (120) may include a manual actuator (124), which is shown in the form of a knob configured to be manually rotated. Manual actuator (124) may engage other components of surgical instrument (110) to serve as a "bailout" mechanism to obtain a desired movement in end effector (116) without powered actuation of drive system (120). Shaft assembly (114) may include additional drive components, such as portions of a drive train (126), that may couple instrument base (112) to a moveable feature (128) of shaft assembly (114) that may be coupled to end effector (116). Shaft assembly (114) may be configured for use with a variety of interchangeable end effectors (116), such as a cutter, grasper, a cautery tool, a camera, a light, or a surgical stapler, for example.

C. First Exemplary End Effector

Figure 6:
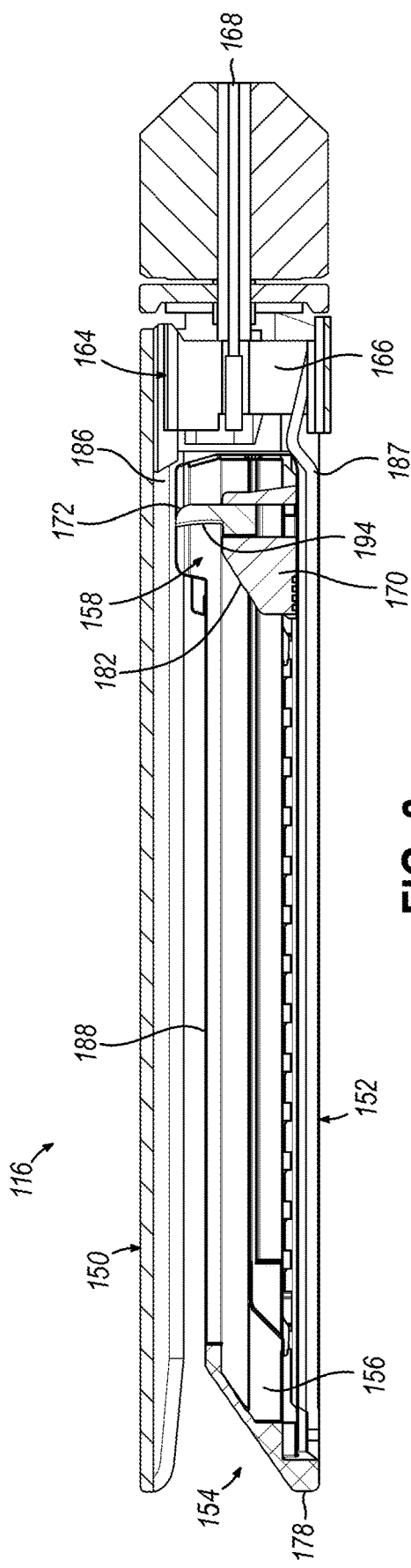
FIG. 6 depicts a side cross-sectional view of the end effector of FIG. 4, where the end effector includes a staple cartridge.

FIG. 6 shows a cross-sectional side view of end effector (116) of surgical instrument (110). End effector (116) extends distally from a distal end of shaft assembly (114). In the present example, end effector (116) comprises a surgical stapler, which may also be referred to herein as an "endocutter," configured to clamp, cut, and staple tissue. As illustrated, end effector (116) includes opposing upper and lower jaws (150, 152) configured to move relative to one another between open and closed positions for clamping and releasing tissue.

One or both of upper and lower jaws (150, 152) may be configured to pivot and thereby actuate end effector (116) between open and closed positions. Lower jaw (152) includes a removable staple cartridge (154). In the illustrated example, lower jaw (152) is pivotable relative to upper jaw (150) to move between an open, unclamped position and a closed, clamped position. In other examples, upper jaw (150) may move relative to lower jaw (152) (e.g., similar to end effector (210) of FIGS. 9-10). In still other examples, both and upper and lower jaws (150, 152) may move to actuate end effector (116) between open and closed positions. In the present example, lower jaw (152) is referred to as a "cartridge jaw" or "channel jaw," and upper jaw (150) is referred to as an "anvil jaw."

Figure 8:
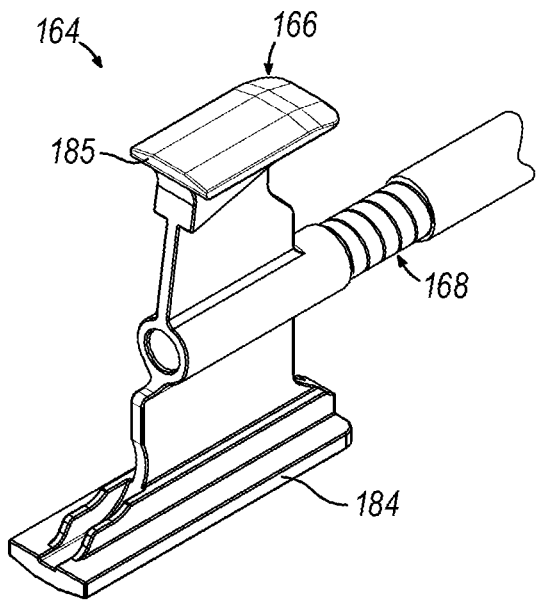
FIG. 8 depicts a driving assembly configured for use with the staple cartridge of FIG. 7.
Figure 9:
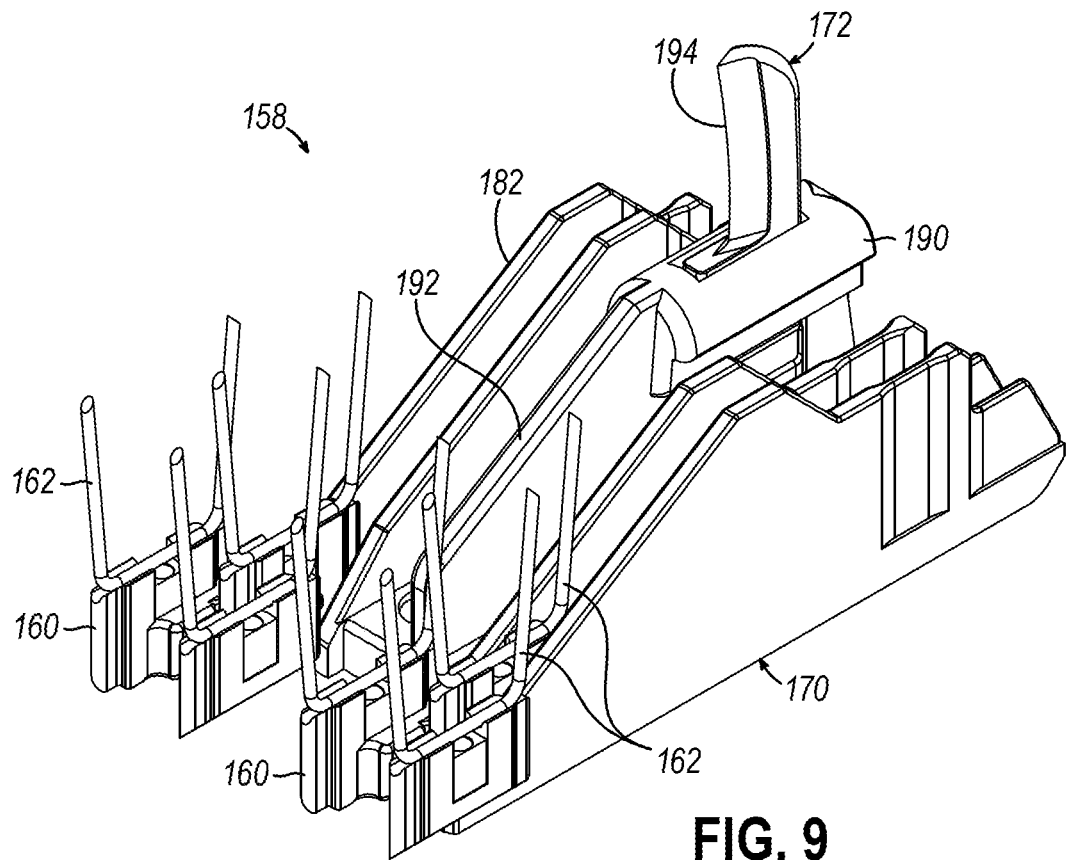
FIG. 9 depicts a firing assembly, staple drivers, and staples configured for use with the staple cartridge of FIG. 7.

Upper jaw (150) defines a surface that has a plurality of pockets (not shown) and operates as an anvil to deform staples ejected from staple cartridge (154) during operation. Staple cartridge (154) is replaceable, for example, by removing a used staple cartridge (154) from end effector (116) and inserting a new staple cartridge (154) into lower jaw (152). Staple cartridge (154) includes a staple cartridge body (156) that houses a firing assembly (158), a plurality of staple drivers (160) (also referred to as staple pushers), and a plurality of staples (162). As shown in FIGS. 6 and 8, end effector (116) includes a driving assembly (164) that includes a pusher member (166) that is operatively coupled with an actuation mechanism via a push rod (168). As shown in FIG. 6 and FIG. 9, firing assembly (158) includes a wedge sled (170) (also referred to as a staple pushing shuttle), and a knife member (172).

Figure 7:
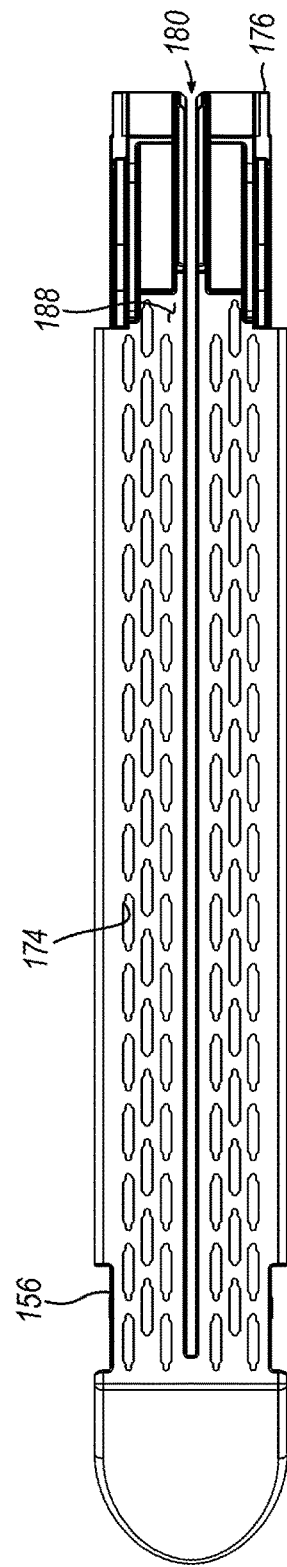
FIG. 7 depicts a top view of a deck of the staple cartridge of FIG. 6.

FIG. 7 shows a top view of staple cartridge body (156). Staple cartridge body (156) includes an array of staple accommodating apertures (174) (also known as openings) extending through an upper deck (188) of staple cartridge body (156). Each aperture (174) slidably houses a respective staple (162) in an unformed state and a free end of a corresponding staple driver (160) positioned beneath the unformed staple (162). Staple cartridge (154) includes proximal and distal ends (176, 178). In operation, staples (162) are sequentially deployed from apertures (174) by staple drivers (160) starting at proximal end (176) and advancing toward distal end (178). A vertical slot (180), configured to accommodate knife member (172), extends through part of staple cartridge (154).

FIG. 8 shows pusher member (166) as including first and second flanges (184, 185). First flange (184) is configured to be received in a longitudinal slot (186) (shown in FIG. 6) of upper jaw (150) and second flange (185) is configured to be received in a longitudinal slot (187) (shown in FIG. 6) of staple cartridge body (156) of lower jaw (152). First and second flanges (184, 185) move along longitudinal slots (186, 187) during actuation of pusher member (166). In some versions, pusher member (166) may include a single flange (e.g., omitting first flange (184)). As shown, longitudinal slot (186) is generally enclosed and longitudinal slot (187) opens to an exterior surface of lower jaw (152).

FIG. 9 shows a perspective view of firing assembly (158), which is configured to be slidably received within the proximal end of staple cartridge body (156) in a longitudinal direction prior to engaging staple drivers (160) and staples (162). Wedge sled (170) of firing assembly (158) slidingly interfaces with staple cartridge body (156). More specifically, wedge sled (170) advances distally along staple cartridge body (156) such that ramp portions (182) of wedge sled contact staple drivers (160). Staple drivers (160) push staples (162) out of apertures (174) of staple cartridge body (156) to penetrate through and staple tissue clamped between staple cartridge body (156) and upper jaw (150). An initial distal actuation of pusher member (166) may move pusher member (166) into contact with wedge sled (170), with further actuation pushing staples (162) transversely out of staple cartridge body (156).

At an initial proximal position of wedge sled (170), knife member (172) is housed within staple cartridge body (156). The position of knife member (172) is controlled during a first portion of the movement of wedge sled (170) from proximal end (176) of staple cartridge body (156) to distal end (178) of staple cartridge (154), so that a cutting edge (194) of knife member (172) extends through vertical slot (180). Vertical slot (180) accommodates cutting edge (194) of knife member (172) as firing assembly (158) is moved toward distal end (178) of staple cartridge (154). Wedge sled (170) includes a guide member (190) that provides a bearing surface that cooperates with a similarly shaped surface of staple cartridge body (156) to guide wedge sled (170). Guide member (190) extends from a vertical rib member (192) of wedge sled (170), which forms a central portion of wedge sled (170). In some versions, knife member (172), or at least cutting edge (194), may be retracted below upper deck (188) of staple cartridge body (156) prior to firing assembly (158) reaching its distal most position adjacent to distal end (178) of staple cartridge (154).

D. Second Exemplary End Effector

Figure 10:
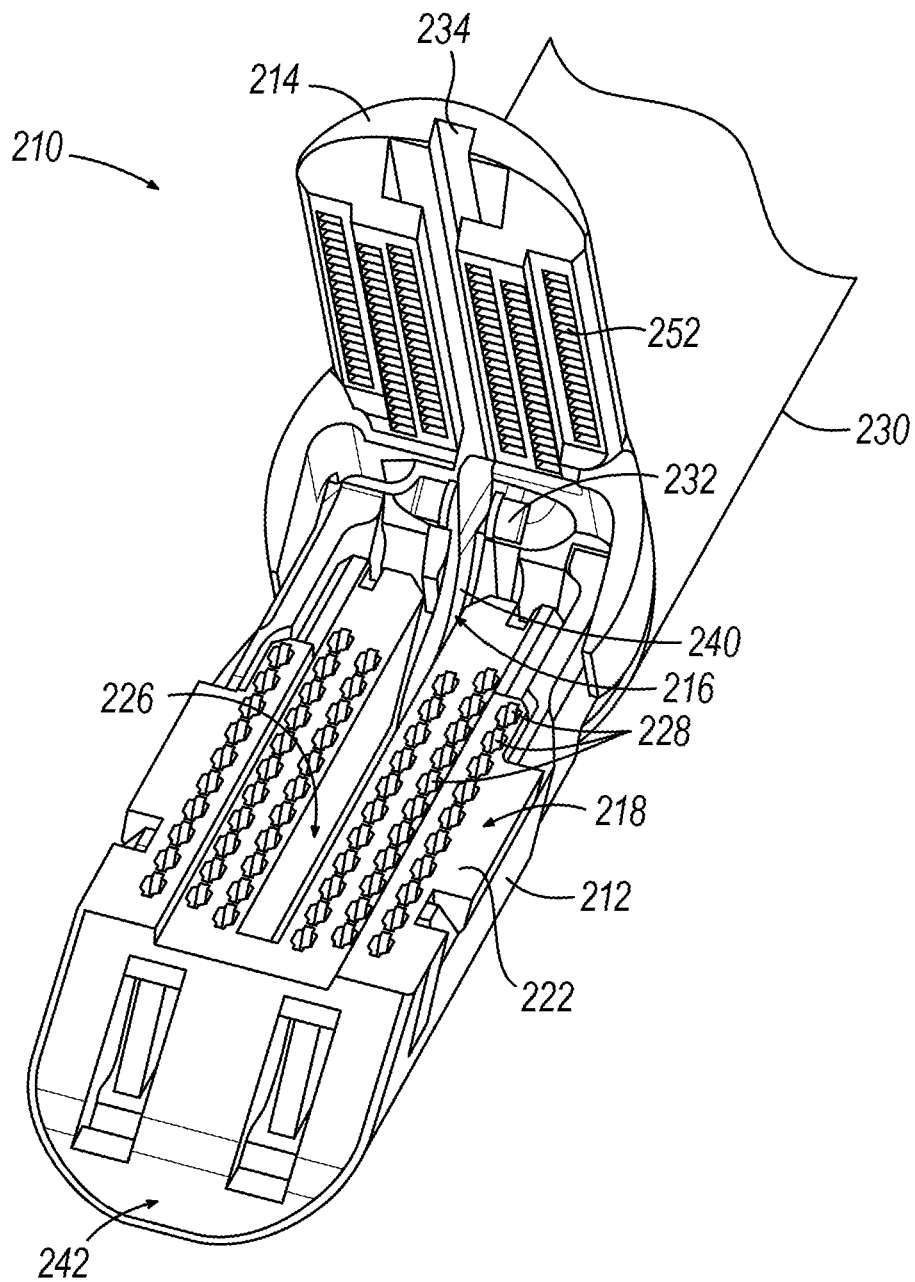
FIG. 10 depicts a second exemplary end effector that may be configured for use with the robotic surgical system of FIG. 1.
Figure 11:
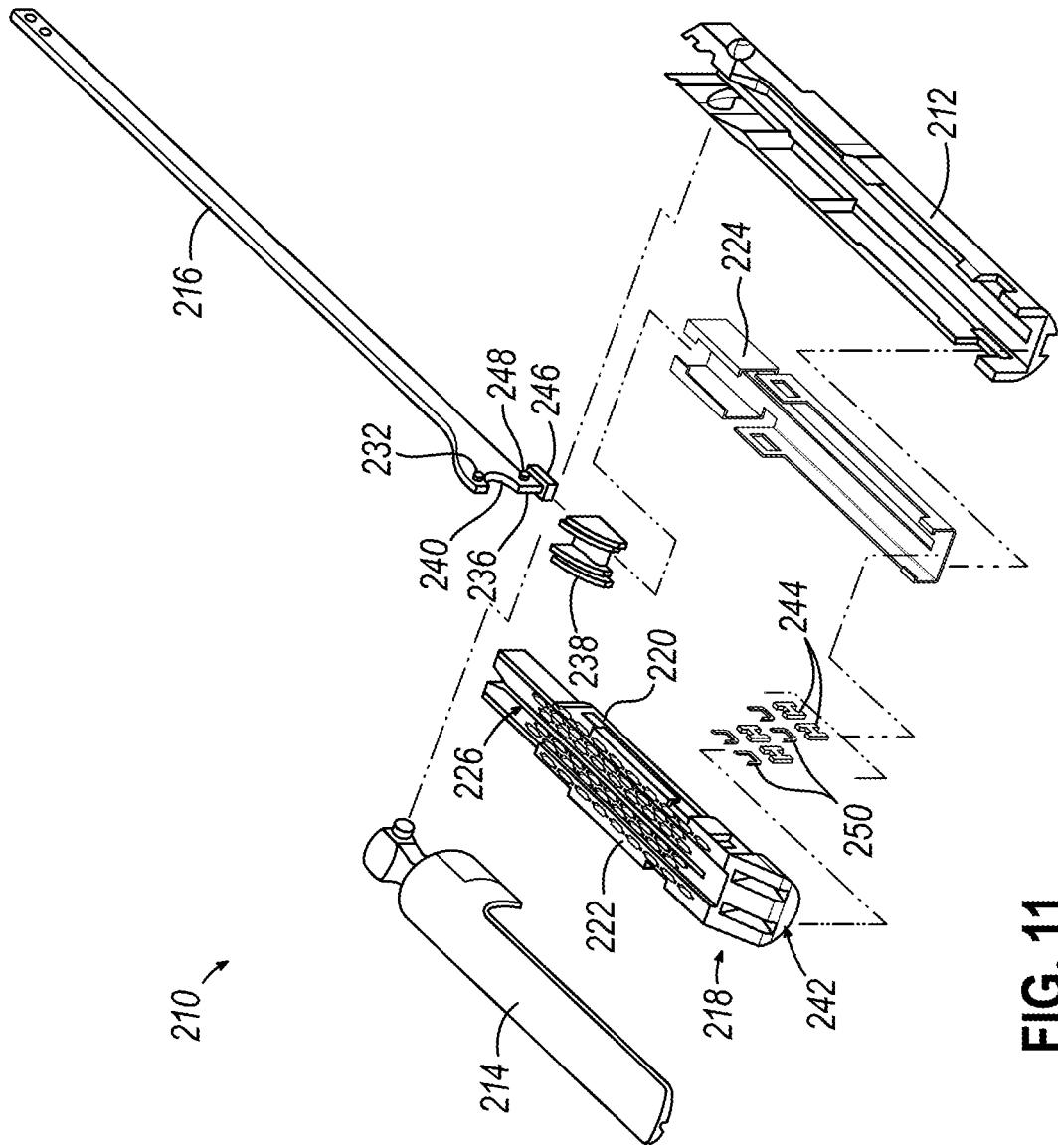
FIG. 11 depicts an exploded view of the end effector of FIG. 10.

FIGS. 10-11 show a second exemplary end effector (210), in an open position, that is configured to compress, cut, and staple tissue. End effector (210) may be configured for use with surgical instrument (110) of FIG. 4, or with surgical instruments of alternative constructions. End effector (210) may be constructed and operable in accordance with at least some of the teachings of U.S. patent application Ser. No. 16/916,295, entitled "Surgical Stapler Cartridge Retainer with Ejector Feature," filed Aug. 3, 2020, the disclosure of which is incorporated by reference herein in its entirety. End effector (210) of the present example includes a lower jaw (212) and an upper jaw in the form of a pivotable anvil (214). Lower jaw (212) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein in its entirety. Anvil (214) may be constructed and operable in accordance with at least some of the teachings of U.S. Pat. No. 10,092,292, entitled "Staple Forming Features for Surgical Stapling Instrument," issued Oct. 9, 2018, the disclosure of which is incorporated by reference herein in its entirety.

FIG. 10 shows end effector (210), where anvil (214) is pivoted to an open position and a firing beam (216) is proximally positioned, allowing an unspent staple cartridge (218) to be removably installed into a channel of lower jaw (212). Staple cartridge (218) includes a cartridge body (220), which presents an upper deck (222) and is coupled with a lower cartridge tray (224). A vertical slot (226) is formed through part of staple cartridge (218) and opens upwardly through upper deck (222). One or more rows of staple apertures (228) are formed through upper deck (222) on one side of vertical slot (226), with one or more rows of staple apertures (228) being formed through upper deck (222) on the other side of vertical slot (226). End effector (210) is closed by distally advancing a closure tube (not shown) and a closure ring (230). Firing beam (216) is then advanced distally so that an upper pin of firing beam (216) enters longitudinal anvil slot (234). Simultaneously, a pusher block (236) located at the distal end of firing beam (216) engages a wedge sled (238) housed within cartridge body (220), such that wedge sled (238) is pushed distally by pusher block (236) as firing beam (216) is advanced distally through staple cartridge (218) and anvil (214).

During firing, cutting edge (240) of firing beam (216) enters vertical slot (226) toward distal end (242) of staple cartridge (218), severing tissue clamped between staple cartridge (218) and anvil (214). As best seen in FIG. 11, wedge sled (238) presents inclined cam surfaces that urge staple drivers (244) upwardly as wedge sled (238) is driven distally through staple cartridge (218). A firing beam cap (246) slidably engages a lower surface of lower jaw (212). Wedge sled (238) is movable longitudinally within staple cartridge (218), while staple drivers (244) are movable vertically within staple cartridge (218). A middle pin (248) and pusher block (236) of firing beam (216) together actuate staple cartridge (218) by entering into vertical slot (226) within staple cartridge (218), driving wedge sled (238) distally into upward camming contact with staple drivers (244) that in turn drive staples (250) out through staple apertures (228) and into forming contact with staple forming pockets (252) on the inner surface of anvil (214). Additional examples of alternative surgical instruments and/or associated features are described in U.S. patent application Ser. No. 16/946,363, entitled "Articulation Mechanisms for Robotic Surgical Tools," filed on Jun. 18, 2020, the disclosure of which is hereby incorporated by reference herein in its entirety.

It will be appreciated that any one or more of the teachings described below may be combined with any one or more of the teachings described above in connection with FIGS. 1-11.

II. Exemplary Bailout Mechanisms for Surgical Instrument

In some examples of drive system (120) of surgical instrument (110) described above, it may be desirable to include certain bailout features to provide manual drive of drive system (120). For instance, during the course of a surgical procedure, unexpected operational conditions may sometimes be encountered. When such conditions are encountered, it may be desirable to immediately terminate or pause the surgical procedure, for example after a distal firing stroke of surgical instrument (110) has initiated. To do so, it may be desirable to actuate one or more portions of surgical instrument (110) manually or without input from robotic surgical system (10). One merely exemplary bailout feature may be a drive to retract an actuation assembly, shown as a driving assembly (164). This bailout feature may be desirable to return firing system components of surgical instrument (110) to a proximal, pre-fired position and enable jaws (150, 152) of end effector (116) to be opened to release the clamped tissue and subsequently withdraw end effector (116) from a patient. This particular bailout feature may be referred to as a manual bailout mechanism in some examples.

In such manual bailout mechanisms, manual drive features may be integrated into robotically controlled drive features. Such a configuration may be desirable to promote a compact and light weight design. However, such integration may lead to a more complex mechanism, which may require more force during manual drive. As a result, it may be desirable to incorporate certain features into such manual bailout mechanisms to promote ease of use during manual operation.

A. Exemplary Bailout Mechanism

Figure 12:
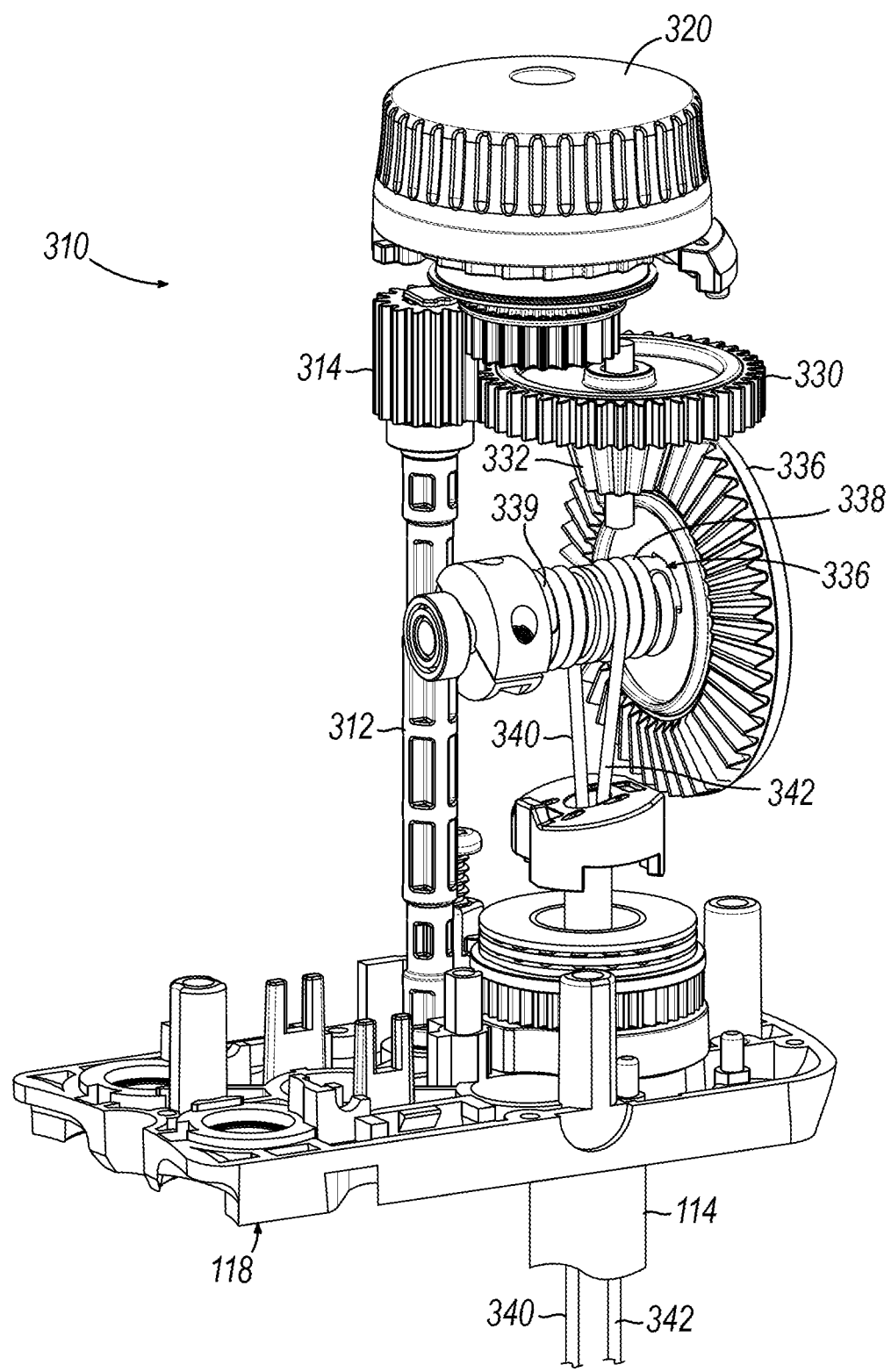
FIG. 12 depicts a perspective view of an exemplary bailout mechanism that may be incorporated into the surgical instrument of FIG. 4.

FIG. 12 shows an exemplary bailout mechanism (310) (also referred to as bailout assembly, opening mechanism, or opening assembly) that may be readily incorporated into drive system (120) of surgical instrument (110) described above. Bailout mechanism (310) is generally configured to drive movement of jaws (150, 152) of end effector (116) between an open and closed configuration using either motor driven input or manual input. Bailout mechanism (310) includes a motor input shaft (312) to facilitate motor input and a manual drive wheel (320) (also referred to as a knob, driver, or manual drive input) to facilitate manual input.

Motor input shaft (312) extends proximally from attachment interface (118). Although not shown, a distal end of motor input shaft (312) may include an input coupler similar to input couplers (130) described above. As with input couplers (130) described above, the input coupler may be configured to engage or otherwise communicate with a corresponding output coupler (not shown) of robotic arm (42) to rotate motor input shaft (312).

A proximal end of motor input shaft (312) includes an input gear (314). Input gear (314) is configured to mesh with a combination drive gear (330). As will be described in greater detail below, input gear (314) is generally configured to transmit rotary input provided by motor input shaft (312) to other components of bailout mechanism (310) to ultimately drive movement of jaws (150, 152) of end effector (116).

Manual drive wheel (320) is generally configured for manual rotation by an operator. In the present example, manual drive wheel (320) extends from the proximal end of bailout mechanism (310) to permit actuation from the proximal end of surgical instrument (110). However, in other examples, manual drive wheel (320) may have a variety of alternative positions relative to surgical instrument (110). The shape of manual drive wheel (320) is generally cylindrical to promote grasping by an operator. To further promote gasping, manual drive wheel (320) may include one or more grasping features such as grooves, knurling, ribs, and/or etc.

A manual drive gear (322) extends distally from manual drive wheel (320). As will be described in greater detail below, manual drive gear (322) is generally configured to communicate a manual rotary input from manual drive wheel (320) to other portions of bailout mechanism (310) to ultimately drive movement of jaws (150, 152) of end effector (116). In some examples, manual drive gear (322) may be integral with manual drive wheel (320) such that any rotatory motion of manual drive wheel (320) is communicated to manual drive gear (322). In other examples, manual drive wheel (320) and manual drive gear (322) may be connected by an intermediate mechanism to modify communication of at least some rotary input of manual drive wheel (320) to manual drive gear (322). By way of example only, one suitable intermediate mechanism may be a ratcheting mechanism to permit drive of manual drive gear (322) when manual drive wheel (320) is rotated in one direction, but prevent drive of manual drive gear (322) when manual drive wheel (320) is rotated in another direction. Of course, various alternative suitable intermediate mechanisms may be used as will be appreciated by those of ordinary skill in the art in view of the teachings herein.

Manual drive gear (322) is in communication with input gear (314). Thus, manual drive gear (322) is configured to transmit rotary motion to input gear (314) from manual drive wheel (320). Input gear (314), in turn, is in communication with a combination drive gear (330). Combination drive gear (330) is configured to drive an integral bevel gear (332), which communicates with a capstan gear (334). Capstan gear (334) defines a bevel complementary to the bevel of bevel gear (332) to promote meshing of the two gears (332, 334). Capstan gear (334) is in communication with a capstan (336), which is configured to rotate with capstan gear (334) to manipulate actuation cables (340, 342).

Capstan (336) defines a shaft extending from capstan gear (334) perpendicularly relative to a longitudinal axis defined by elongate shaft (114) of surgical instrument (110). Capstan (336) is configured as a double capstan and defines two spool channels (338, 339) configured to receive actuation cables (340, 342) in a helical pattern. In particular, capstan (336) defines a first spool channel (338) having a first pitch and a second spool channel (339) having a second pitch. In the present example, the first pitch and the second pitch are opposite of each other to promote an opposite threading for each actuation cable (340, 342). As a consequence, rotation of capstan (336) in one direction may pull a portion of one actuation cable (340, 342) toward capstan (336), while releasing a portion of another actuation cable (342, 340) to move away from capstan (336).

Actuation cables (340, 342) extend distally away from capstan (336) and into elongate shaft (114) of surgical instrument (110). In the present example, bailout mechanism (310) includes a retraction actuation cable (340) and an advancement actuation cable (342). As will be described in greater detail below, retraction actuation cable (340) and advancement actuation cable (342) are together configured to manipulate structures within elongate shaft (114) to control movement of end effector (116) using rotation of capstan (336) via motor input shaft (312) or manual drive wheel (320).

Figure 13:
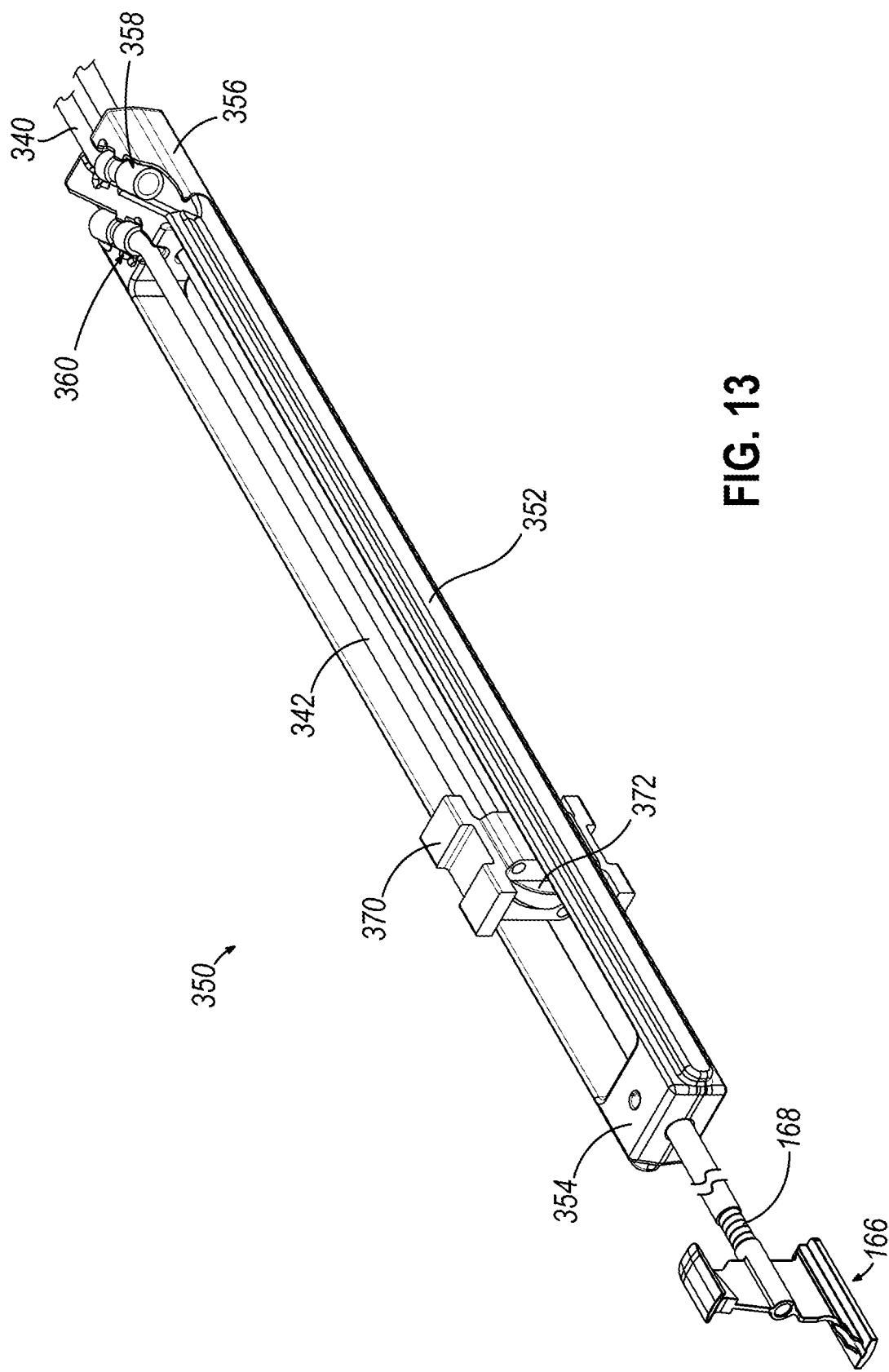
FIG. 13 depicts a perspective view of a shuttle of the bailout mechanism of FIG. 12.
Figure 14:
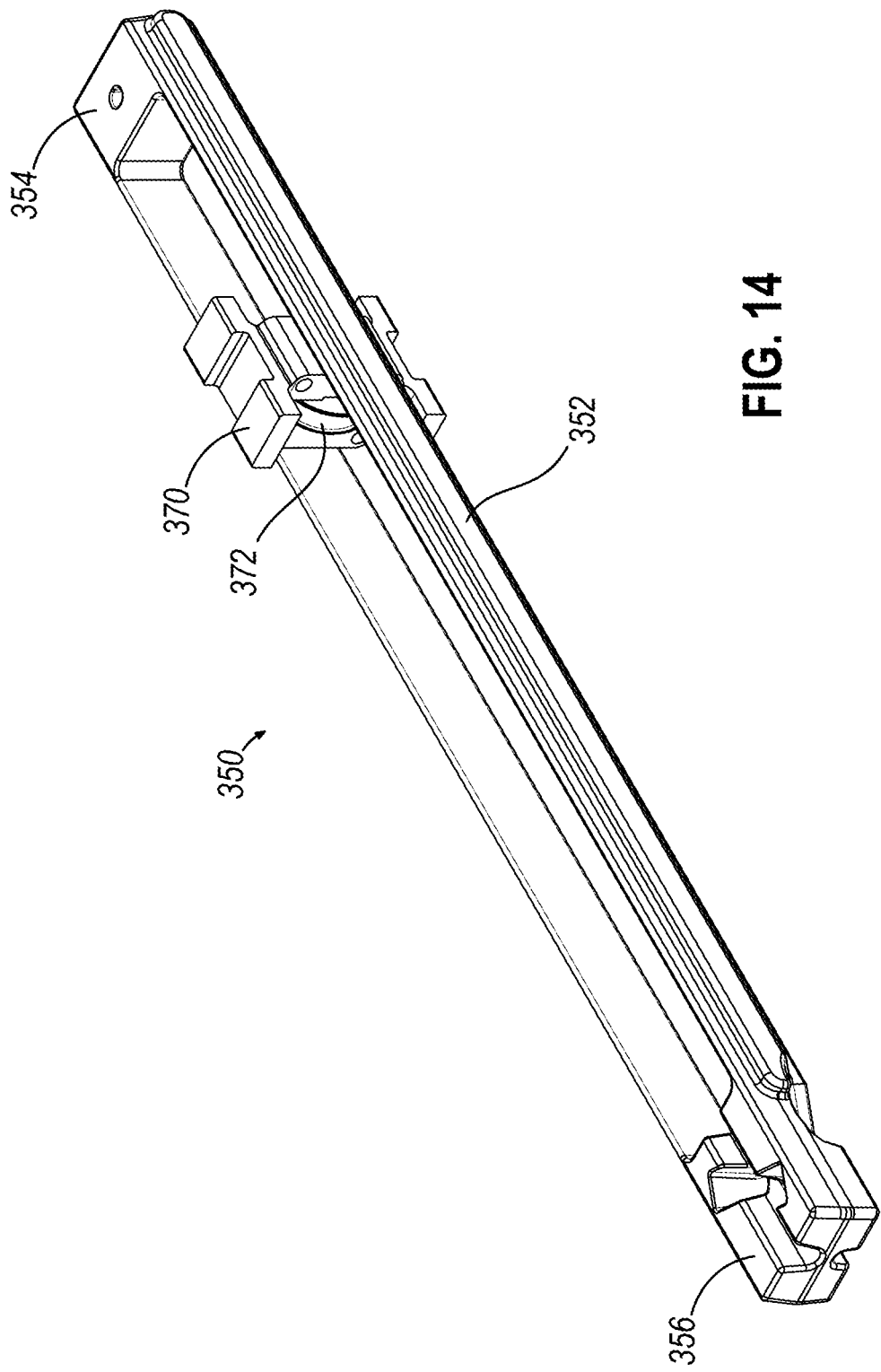
FIG. 14 depicts another perspective view of the shuttle of FIG. 13.

As best seen in FIGS. 13 and 14, bailout mechanism (310) further includes a shuttle (350), which may be disposed within elongate shaft (114) of surgical instrument (110). Shuttle (350) is generally configured to translate within elongate shaft (114) to drive movement of end effector (116). In particular, shuttle (350) includes an elongate frame (352) having a manipulation end (354) and a coupling end (356). Manipulation end (354) is in communication with pusher rod (168) to drive movement pusher member (166), which may be configured to manipulate lower jaw (152) relative to upper jaw (150). Thus, shuttle (350) is configured to manipulate jaws (150, 152) by translating within elongate shaft (114) to push and pull push rod (168).

As noted above, movement of jaws (150, 152) may be controlled by actuation cables (340, 342). Thus, shuttle (350) of the present example is configured to engage actuation cables (340, 342) to facilitate translation of shuttle (350) within elongate shaft (114) via actuation cables (340, 342). Specifically, coupling end (356) of shuttle (350) is configured to couple to each end of actuation cable (340, 342). As best seen in FIGS. 13 and 14, coupling end (356) includes a retraction receiver (358) and an advancement receiver (360). Retraction receiver (358) is configured to receive retraction actuation cable (340). Similarly, advancement receiver (360) is configured to receive advancement actuation cable (342).

Retraction receiver (358) and advancement receiver (360) are oriented in opposite directions to permit application of different force vectors to shuttle (350). For instance, retraction receiver (358) is oriented proximally to permit retraction actuation cable (340) to pull shuttle distally (350). Similarly, advancement receiver (360) is oriented distally to permit advancement actuation cable (342) to pull shuttle proximally with the assistance of other portions of shuttle (350) described in greater detail below.

Bailout mechanism (310) further includes a block (370) disposed within elongate frame (352) of shuttle (350). Block (370) includes a pully (372) configured to receive advancement actuation cable (342). Specifically, pully (372) is configured to reverse the direction of advancement actuation cable (342) such that advancement actuation cable (342) may pass through coupling end (356) of shuttle (350), reverse at pully (372), and then return to coupling end (356) to couple to advancement receiver (360). The configuration of pully (372) and coupling end (356) is generally desirable to permit advancement actuation cable (342) to pull shuttle (350) distally using tension provided by capstan (336).

Block (370) of the present example is not physically secured to shuttle (350). In other words, shuttle (350) may move relative to block (370). Although not shown, it should be understood that block (370) may be secured or otherwise mechanically grounded to elongate shaft (114). This configuration may be desirable to increase the mechanical advantage of advancement actuation cable (342) and pully (372). In other examples, block (370) may be secured directly to shuttle (350) to provide similar functionality without added mechanical advantage.

Returning to FIG. 12, in an exemplary use, bailout mechanism (310) may receive input from either motor input shaft (312) or manual drive wheel (320). In both uses, this may result in turning of input gear (314) either by motor input shaft (312) directly or manual drive gear (322).

Rotation of input gear (314) by wither motor input shaft (312) or manual drive gear (322) may result in rotation of combination drive gear (330). Rotation of combination drive gear (330) rotates bevel gear (332), which rotates capstan gear (334). As a result of rotation of capstan gear (334), capstan (336) likewise rotates. One actuation cable (340, 342) will then be tensioned and another actuation cable (342, 340) will be relaxed, depending on the direction of rotation of capstan (336).

As shown in FIGS. 13 and 14, translation of shuttle (350) may be controlled by tensioning or relaxing a given actuation cable (340, 342). For instance, if capstan (336) is rotated to tension retraction actuation cable (340), retraction actuation cable (340) will pull directly on coupling end (356) of shuttle (350) to translate shuttle (350) proximally. This proximal translation of shuttle (350) will pull pusher member (166) proximally and thereby open jaws (150, 152).

Alternatively, if capstan (336) is rotated in an opposite direction to tension advancement actuation cable (342), the tension on advancement actuation cable (342) will be directed through pully (372) and then to coupling end (356) to pull shuttle (350) distally. This distal translation of shuttle (350) will push pusher member (166) distally and thereby close jaws (150, 152).

B. Exemplary Bailout Mechanism with Improved Retraction Feature

Figure 15:
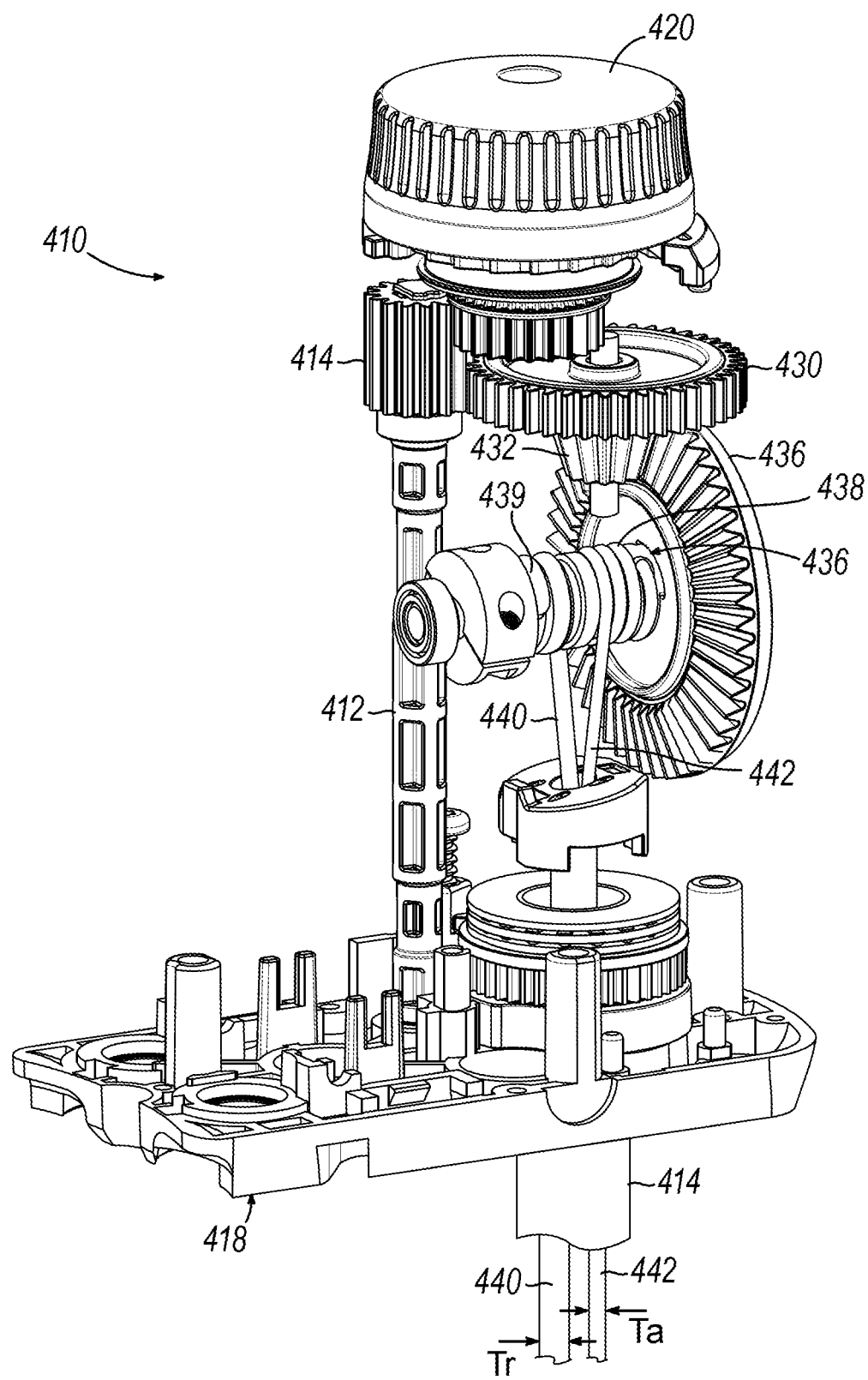
FIG. 15 depicts a perspective view of another exemplary bailout mechanism that may be incorporated into the surgical instrument of FIG. 4.

FIG. 15 shows an exemplary alternative bailout mechanism (410) (also referred to as bailout assembly, opening mechanism, or opening assembly) that may be readily incorporated into drive system (120) of surgical instrument (110) described above. Bailout mechanism (410) is substantially similar to bailout mechanism (310) described above. For instance, like with bailout mechanism (310) described above, bailout mechanism (410) of the present example is generally configured to drive movement of jaws (150, 152) of end effector (116) between an open and closed configuration using either motor driven input or manual input. As such, bailout mechanism (410) of the present example includes a motor input shaft (412) and a manual drive wheel (420) (also referred to as a knob, driver, or manual drive input) to facilitate manual input.

As with motor input shaft (312) described above, motor input shaft (412) of the present example extends proximally from attachment interface (118) and includes an input gear (414) similar to input gear (314) described above. Input gear (414) is configured to mesh with a combination drive gear (430), which may be used to drive other components of bailout mechanism (410), as will be described in greater detail below.

Manual drive wheel (420) is substantially similar to manual drive wheel (320) described above in that manual drive wheel (420) is generally configured for manual rotation by an operator. Thus, the shape of manual drive wheel (420) is generally cylindrical to promote grasping by an operator. Also like manual drive wheel (320) described above, manual drive wheel (420) of the present example includes a manual drive gear (422) extending distally therefrom.

Manual drive gear (422) is in communication with input gear (414). Thus, manual drive gear (422) is configured to transmit rotary motion to input gear (414) from manual drive wheel (420). Input gear (414), in turn, is in communication with a combination drive gear (430). Combination drive gear (430) is configured to drive an integral bevel gear (432), which communicates with a capstan gear (434). Capstan gear (434) defines a bevel complementary to the bevel of bevel gear (432) to promote meshing of the two gears (332, 434). Capstan gear (434) is in communication with a capstan (436), which is configured to rotate with capstan gear (434) to manipulate actuation cables (440, 442).

Capstan (436) of the present example is substantially similar to capstan (436) described above. For instance, capstan (436) defines a shaft extending from capstan gear (434) perpendicularly relative to a longitudinal axis defined by elongate shaft (114) of surgical instrument (110). Capstan (436) is configured as a double capstan and defines two spool channels (438, 439) configured to receive actuation cables (440, 442) in a helical pattern. As similarly described above, spool channels (438, 439) include a first spool channel (438) having a first pitch and a second spool channel (439) having a second pitch. The first pitch and the second pitch are opposite of each other to promote an opposite threading for each actuation cable (440, 442). As a consequence, rotation of capstan (436) in one direction may pull a portion of one actuation cable (440, 442) toward capstan (436), while releasing a portion of another actuation cable (442, 440) to move away from capstan (436).

Actuation cables (440, 442) extend distally away from capstan (436) and into elongate shaft (114) of surgical instrument (110). In the present example, bailout mechanism (410) includes a retraction actuation cable (440) and an advancement actuation cable (442). As with retraction actuation cable (340) and advancement actuation cable (342) described above, retraction actuation cable (440) and advancement actuation cable (442) of the present example are together configured to manipulate structures within elongate shaft (114) to control movement of end effector (116) using rotation of capstan (436) via motor input shaft (412) or manual drive wheel (420).

Unlike retraction actuation cable (340) and advancement actuation cable (342) described above, retraction actuation cable (440) and advancement actuation cable (442) of the present example define differing diameters or thicknesses. In particular, retraction actuation cable (440) of the present example defines a diameter ($T_r$) that is greater than a diameter ($T_a$) defined by advancement actuation cable (442). This configuration may be desirable in some circumstances to promote the physical integrity of bailout mechanism (410). For instance, in some circumstances, a relatively large load may be applied to jaws (150, 152) of end effector (116) by tissue, bone, or other structures proximate end effector (116). Such a load may resist movement of jaws (150, 152) from a closed to open configuration. As a result, it may be beneficial for retraction actuation cable (440) to withstand relatively high loads to move jaws (150, 152) from the closed configuration to the open configuration in such circumstances.

Although the present example promotes physical integrity of bailout mechanism (410) using an increased diameter of retraction actuation cable (440) relative to advancement actuation cable (442) (e.g., $T_r > T_a$), such benefits may be achieved by varying other physical properties of actuation cables (440, 442). For instance, in some examples, retraction actuation cable (440) may be of a different material relative to advancement action cable (442) (e.g., INCONEL versus stainless steel). In other examples, actuation cables (440, 442) may be of the same material but of a different configuration. For instance, in some examples, both actuation cables (440, 442) may be braided, but retraction actuation cable (440) may have a higher strength braid relative to advancement actuation cable (442). In still other examples, various combinations of different physical properties may be used to promote physical integrity of bailout mechanism (410). In addition, or in the alternative, retraction actuation cable (440) may be independently manipulated in some examples such that retraction actuation cable (440) is configured as an independent direct pull cable.

Figure 16:
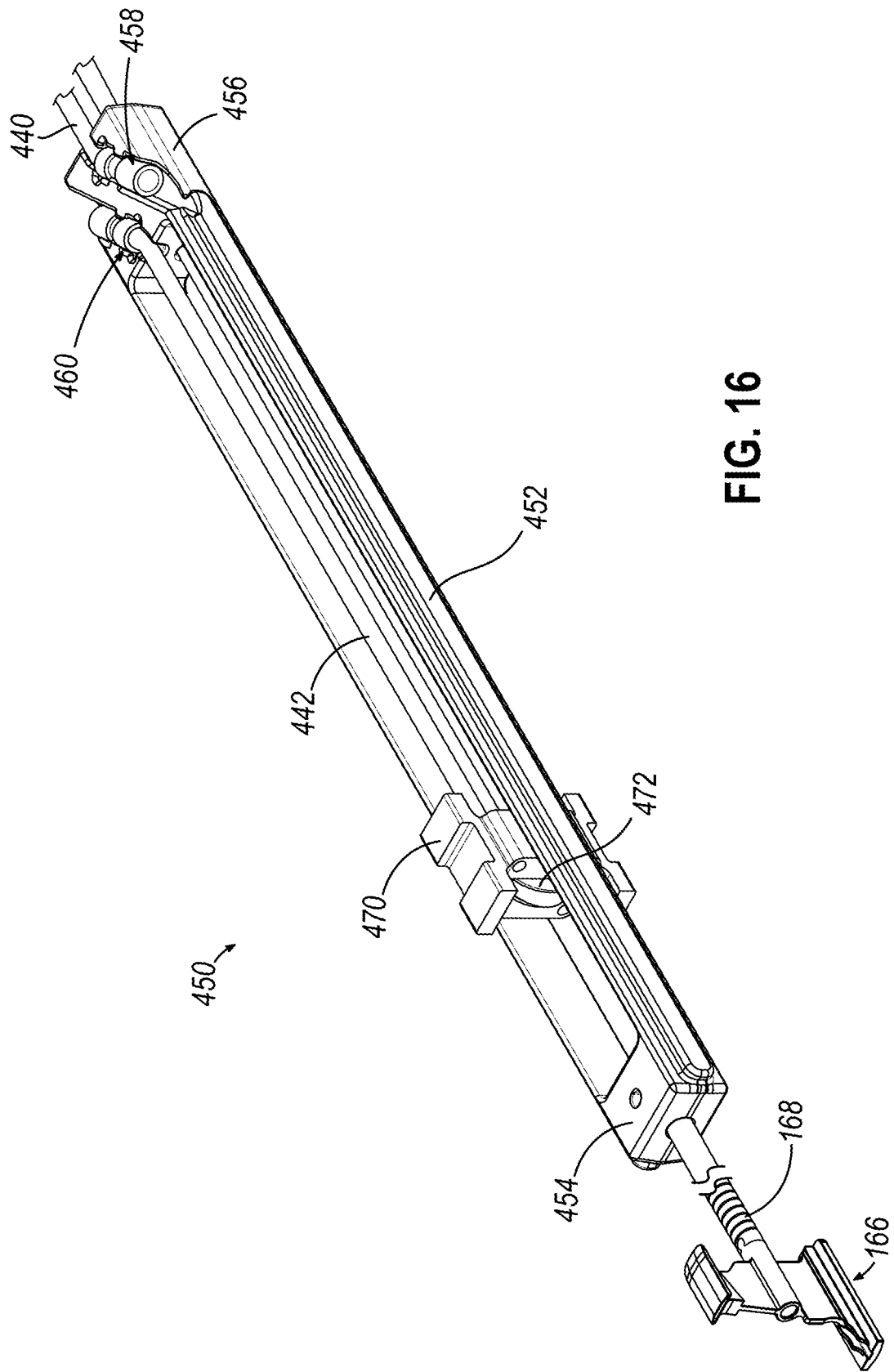
FIG. 16 depicts a perspective view of a shuttle of the bailout mechanism of FIG. 15.

As best seen in FIG. 16, bailout mechanism (410) further includes a shuttle (450), which may be disposed within elongate shaft (114) of surgical instrument (110). Shuttle (450) is substantially similar to shuttle (350) described above. For instance, shuttle (450) of the present example generally configured to translate within elongate shaft (114) to drive movement of end effector (116). As with shuttle (350) described above, shuttle (450) of the present example includes an elongate frame (452) having a manipulation end (454) and a coupling end (456). Manipulation end (454) is in communication with pusher rod (168) such that shuttle (450) is configured to manipulate jaws (150, 152) by translating within elongate shaft (114) to push and pull pusher rod (168).

Figure 17:
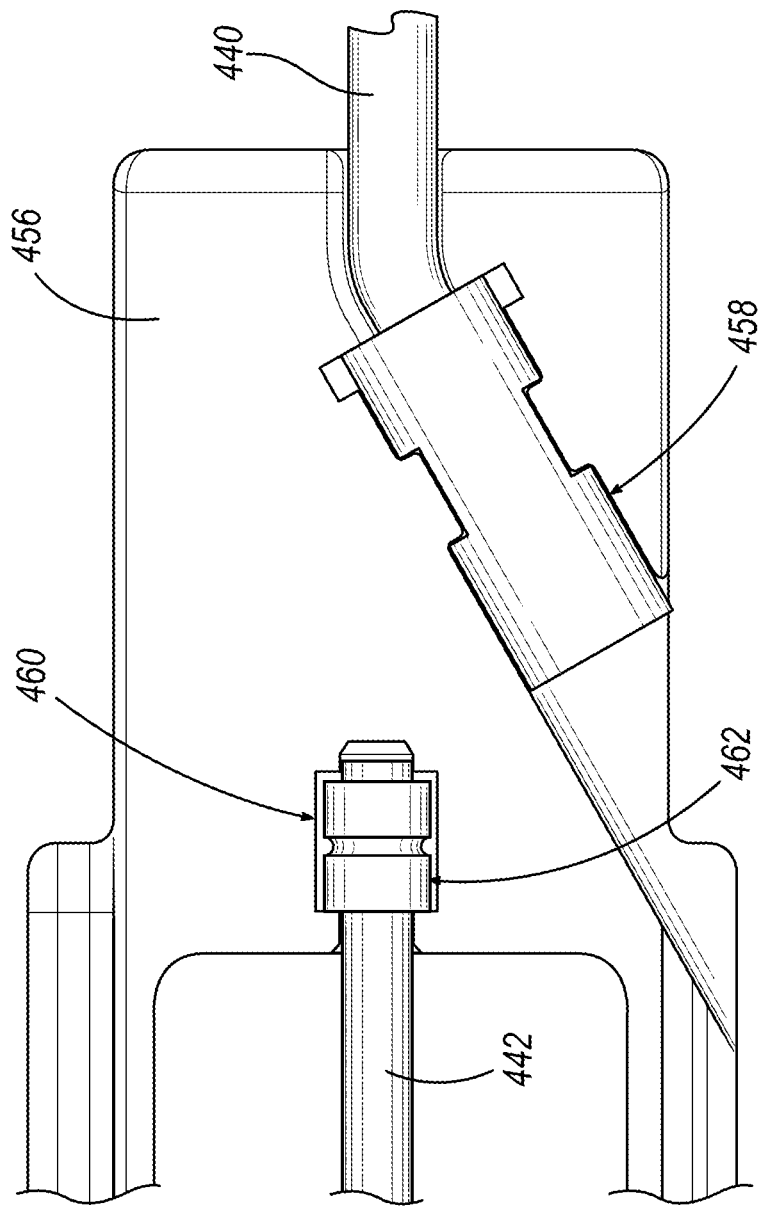
FIG. 17 depicts a partial top plan view of the shuttle of FIG. 16.

Coupling end (456) of shuttle (450) is configured to couple to each end of actuation cable (440, 442). As best seen in FIG. 17, coupling end (456) includes a retraction receiver (458) and an advancement receiver (460). Retraction receiver (458) is configured to receive retraction actuation cable (440). Similarly, advancement receiver (460) is configured to receive advancement actuation cable (442). Although actuation cables (440, 442) of the present example couple to coupling end (456) of shuttle (450), it should be understood that in some examples, one or more of actuation cables (440, 442) may bypass shuttle (450) entirely and coupled directly to pusher member (166). For instance, in some examples, retraction actuation cable (440) may couple directly to pusher member (166) with retraction actuation cable (440) being configured to directly pull pusher member (166).

Unlike coupling end (356) described above, coupling end (456) of the present example includes a release feature (462) associated with advancement receiver (460). Release feature (462) of the present example is configured to couple advancement actuation cable (442) to coupling end (456) until a predetermined load is applied to advancement actuation cable (442), at which point release feature (462) is configured to release advancement actuation cable (442). In other words, release feature (462) is configured to operate as a mechanical fuse to release advancement actuation cable (442) from coupling end (456) upon the application of a load exceeding a predetermined threshold to advancement actuation cable (442). This configuration may be desirable to promote ease of use for bailout mechanism (410) during certain circumstances. For instance, when encountering some bailout conditions, relatively large force may be required to fully close jaws (150, 152). In such circumstances, advancement actuation cable (442) may automatically release to prevent closure of jaws (150, 152) beyond certain predetermined force limits. Meanwhile, retraction actuation cable (440) may remain attached to coupling end (456) to permit proximal translation of shuttle (450) for opening of jaws (150, 152), while preventing distal translation of shuttle (450) for closure of jaws (150, 152).

Release feature (462) of the present example includes a collar configured to release from advancement actuation cable (442) upon application of a predetermined load. The collar may be crimped or swaged to an end of advancement actuation cable (442) to promote fastening until the collar releases. Alternatively, some examples a portion of coupling end (456) may be configured to release advancement actuation cable (442). For instance, coupling end (456) may include a lug or other feature configured to release upon application of a predetermined load. In such examples, the collar may remain coupled to advancement actuation cable (442) upon release thereof.

Bailout mechanism (410) further includes a block (470) disposed within elongate frame (452) of shuttle (450). Block (470) of the present example is substantially similar to block (370) described above. For instance, like block (370), block (470) of the present example includes a pully (472) configured to receive advancement actuation cable (442) and reverse the direction of advancement actuation cable (442). Also like block (370) described above, block (470) of the present example may move relative to shuttle (450) and may be secured or otherwise mechanically grounded to elongate shaft (114). As noted above, this configuration may be desirable to increase the mechanical advantage of advancement actuation cable (442) and pully (472). In other examples, block (470) may be secured directly to shuttle (450) to provide similar functionality without added mechanical advantage.

It should be understood that block (470) and pully (472) in the present example is merely one example of a block and tackle mechanism that might be used to increase the mechanical advantage of either actuation cables (440, 442). Thus, even though the present example includes one block (470) having one pully (472), it should be understood that in other examples, multiple blocks (470) with one pully (472), multiple blocks (470) with multiple pullies (472), or one block (470) with multiple pullies (472) may be used to increase the force applied by either actuation cable (440, 442) or both. In merely one example, a similar block and tackle mechanism may be associated with retraction actuation cable (440). Such a block and tackle may define multiple synchronized loops of retraction actuation cable (440) to magnify the retraction force applied by retraction actuation cable (440). Of course, various other suitable configurations of block and tackle mechanisms will be apparent to those of ordinary skill in the art in view of the teachings herein.

As shown in FIG. 18, in some examples, pusher member (166) may be coupled to push rod (168) using an axial strengthening feature (490). Axial strengthen feature (490) is generally configured to strengthen the interface between pusher member (166) and push rod (168) to resist separation between the two during relatively high axial loads (e.g., during proximal retraction of pusher member (166)). Axial strengthening feature (490) may take on a variety of forms suitable to withstand relatively high axially loads. For instance, in the present example, axial strengthening feature (490) include a mating keyed interface having a rounded key that may be received in a corresponding opening. In other examples, a threaded projection may be received in a threaded bore. In other examples, axial strengthening feature (490) may include a coupler. In still other examples, pusher member (166) and push rod (168) may instead be welded to each other. Of course, axial strengthening feature (490) of the present example is merely optional and may be omitted in some examples.

In use, bailout mechanism (410) of the present example functions similarly to bailout mechanism (310) described above. For instance, capstan (436) may be rotated in a first direction by either motor input shaft (412) or manual drive wheel (420) to tension advancement actuation cable (442) and simultaneously relax retraction actuation cable (440) for advancement of shuttle (450) distally and closure of jaws (150, 152). Similarly, capstan (436) may be rotated in an opposite second direction by either motor input shaft (412) or manual drive wheel (420) to tension retraction actuation cable (440) and simultaneously relax advancement actuation cable (442) for retraction of shuttle (450) proximally and opening of jaws (150, 152).

Unlike bailout mechanism (310) described above, the present use of bailout mechanism (410) may deviate upon an operator encountering unexpected operating conditions. For instance, in some circumstances external structures such as tissue, bone, other surgical instruments or equipment, and/or etc. may add additional forces to jaws (150, 152) either preventing complete closure or resisting opening of jaws (150, 152). In such circumstances, it may be beneficial to open jaws (150, 152) to move or reposition surgical instrument (110). As described above, jaws (150, 152) may be opened by retracting shuttle (450) proximally via rotation of capstan (436) to tension retraction actuation cable (440). Due to the diameter ($T_r$) of retraction actuation cable (440), retraction actuation cable (440) may be used to apply additional force to shuttle (450) and thus jaws (150, 152).

Also during use, excessive application of force to advancement actuation cable (442) may result in release feature (462) releasing advancement actuation cable (442) from coupling end (456) of shuttle (450). As a result, distal translation of shuttle (450) may be disabled, thereby permitting only proximal translation of shuttle (450) via retraction actuation cable (440). In addition, releasing of advancement actuation cable (442) may release any tension applied to shuttle (450) in the distal direction opposite the force applied by retraction actuation cable (440), thereby reducing the force required for retraction actuation cable (440) to translate shuttle (450) proximally.

III. Exemplary Alternative Manual Drivers

In some circumstances, a bailout mechanism similar to bailout mechanisms (310, 410) described above may be operated manually by an operator using a manual input driver similar to manual drive wheels (320, 420) described above. However, in some circumstances, a limiting factor on operation of such bailout mechanisms may be the ability to apply force to the manual input driver. Additionally, in some circumstances, another limiting factor may be the direction of the application of force to the manual input driver. Thus, it may be desirable to incorporate features into such manual input drivers to increase a user's ability to apply force or to ensure the force is applied in a particular direction.

A. Exemplary Alternative Manual Drive Wheel with Arm

FIG. 19A shows an exemplary alternative manual drive wheel (520) (also referred to as a knob, driver, or manual drive input), which may be readily incorporated into bailout mechanisms (310, 410) described above. Manual drive wheel (520) is generally configured to enhance the ability of an operator to apply torque and/or power to manual drive wheel (520), thereby enhancing the ability to drive bailout mechanisms (310, 410). Manual drive wheel (520) is similar to manual drive wheels (320, 420) described above in that manual drive wheel (520) defines a generally cylindrical shape suitable for grasping and may additionally include one or more gripping features to enhance an operator's grip. Although not shown, it should be understood that manual drive wheel (520) may be in communication with one or more gears similar to manual drive gears (322, 422) described above to transmit power from manual drive wheel (520) to other components of bailout mechanisms (310, 410).

Unlike manual drive wheels (320, 420) described above, manual drive wheel (520) of the present example includes an arm (524) (alternatively referred to as a lever) configured to extend and retract relative to a portion of manual drive wheel (520) to provide additional leverage for rotation of manual drive wheel (520). In particular, arm (524) is configured to pivot, flip or rotate from a retracted configuration shown in FIG. 19A to an extended configuration shown in FIG. 19B.

Arm (524) in the present example defines a length approximately corresponding to the diameter of manual drive wheel (520). Additionally, manual drive wheel (520) defines a channel (526) configured to receive arm (524). Channel (526) approximately corresponds to the thickness of arm (524) to permit arm (524) to be relatively flush with the top of manual drive wheel (520) when arm (524) is in the retracted configuration.

One side of arm (524) may be coupled to a portion of manual drive wheel (520) by a hinge, pivot shaft, living hinge, or other feature to promote pivoting, flipping or rotation of arm (524) relative to a portion of manual drive wheel (520). Meanwhile, an opposite end of arm (524) remains free for manipulation by an operator. This permits arm (524) to pivot about the coupling to increase the leverage provided by manual drive wheel (520) by 2 times or more. Although arm (524) of the present example is shown as using a pivoting, flipping or rotational action, it should be understood that other examples may include different configurations to provide extension of arm (524). For instance, in some examples, channel (526) may include a track or other feature to permit arm (524) to slide laterally out relative to a portion of manual drive wheel (520). Still other configurations for extension of arm (524) will be apparent to those of ordinary skill in the art in view of the teachings herein.

To enhance grip of arm (524) the exterior of arm (524) may optionally include one or more grip features. Such grip features may take on a variety of forms such as indentations, protrusions, knurling, and/or etc. Additionally, in some examples such grip features may match grip features incorporated into the perimeter of the cylindrical portion of manual drive wheel (520). In other examples, the grip features may be varied relative to those of manual drive wheel (520).

In use, arm (524) may initially be stowed in the retracted configuration as shown in FIG. 19A. In this configuration, manual drive wheel (520) may be used similar to manual drive wheels (320, 420) described above. Specifically, an operator may grasp manual drive wheel (520) and rotate manual drive wheel (520) about an axis of rotation. Use of manual drive wheel (520) while arm (524) is in the retracted position may be desirable where limited force input is required or in circumstances where there is limited operational clearance between manual drive wheel (520) and other medical components or equipment.

In some contexts, it may be desirable to exert additional force on manual drive wheel (520). To assist with this, an operator may move arm (524) from the retracted configuration shown in FIG. 19A to the extended configuration shown in FIG. 19B. In the present example, arm (524) may be moved to the extended configuration by gasping the uncoupled end thereof and pivoting, flipping, or rotating arm (524) to the position shown in FIG. 19B. In this position, arm extends from the cylindrical perimeter of manual drive wheel (520) by about the diameter of manual drive wheel (520). Thus, an operator may rotate manual drive wheel (520) by applying a force to arm (524). Because of the length of arm (524), additional leverage is provided for increased torque.

Although not shown, in some examples, manual drive wheel (520) may be in communication with a ratcheting mechanism. In such examples, manual drive wheel (520) may be used either with arm (524) in the retracted configuration or the extended configuration to move repeatedly through a desired range of motion. In use, this repeated motion provided by such a ratcheting mechanism may be desirable to make it easier for an operator to apply force to manual drive wheel (520). This benefit may be especially present with arm (524) in the extended configuration, as it may permit an operator to avoid adjusting grip on arm (524) by not having to durn manual drive wheel (520) through a complete rotation.

Figure 20:
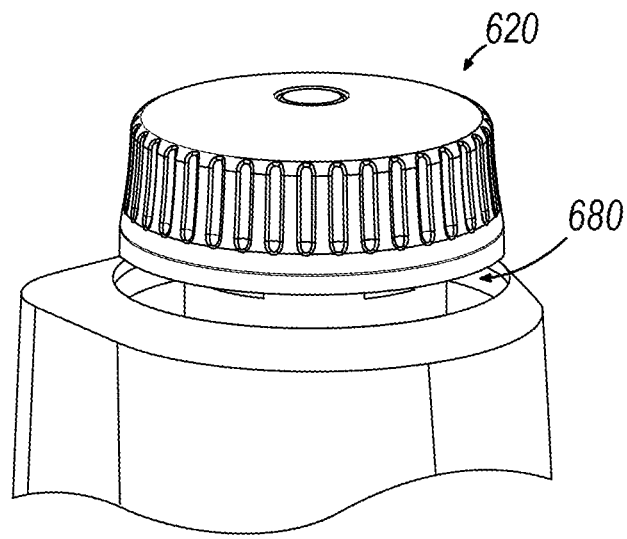
FIG. 20 depicts a perspective view of another manual drive wheel that may be incorporated into the bailout mechanisms of FIG. 12 or 13.

B. Exemplary Alternative Manual Drive Wheel with Instrument Retaining Feature FIG. 20 shows an exemplary alternative manual drive wheel (620) (alternatively referred to as a knob, driver, or manual drive input), which may be readily incorporated into bailout mechanisms (310, 410) described above. Manual drive wheel (620) is generally configured to enhance the ability of an operator to apply torque and/or power to manual drive wheel (620), thereby enhancing the ability to drive bailout mechanisms (310, 410). Manual drive wheel (620) is similar to manual drive wheels (320, 420) described above in that manual drive wheel (620) defines a generally cylindrical shape suitable for grasping and may additionally include one or more gripping features to enhance an operator's grip. Although not shown, it should be understood that manual drive wheel (620) may be in communication with one or more gears similar to manual drive gears (322, 422) described above to transmit power from manual drive wheel (620) to other components of bailout mechanisms (310, 410).

Figure 21:
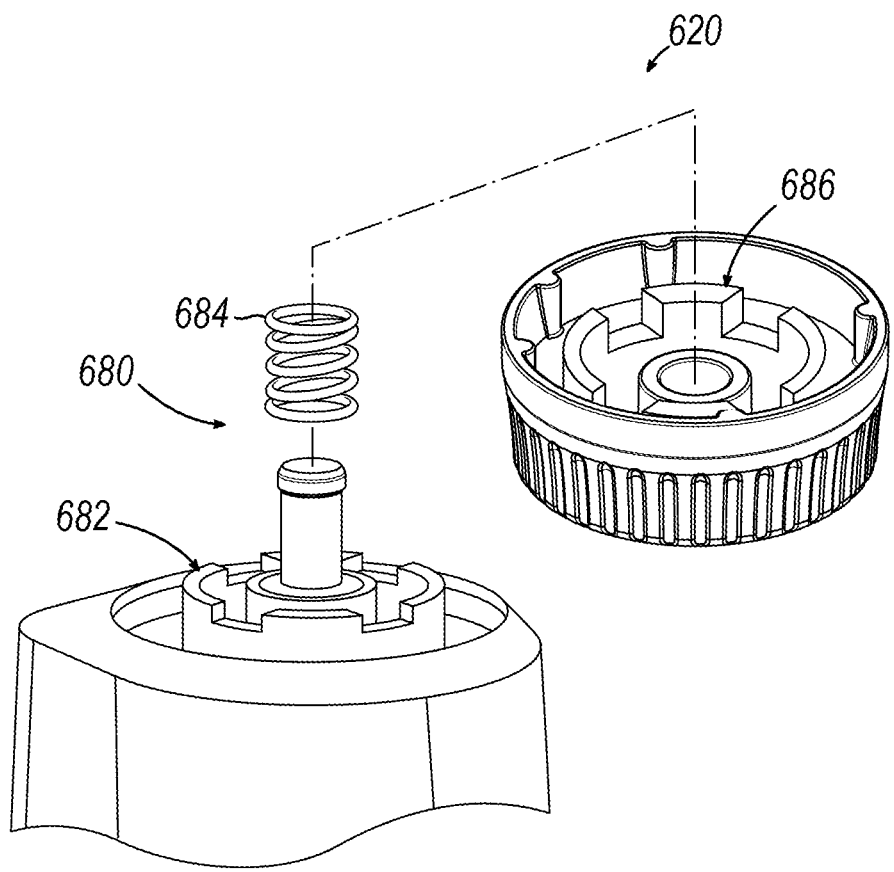
FIG. 21 depicts an exploded perspective view of the manual drive wheel of FIG. 20.
Figure 22:
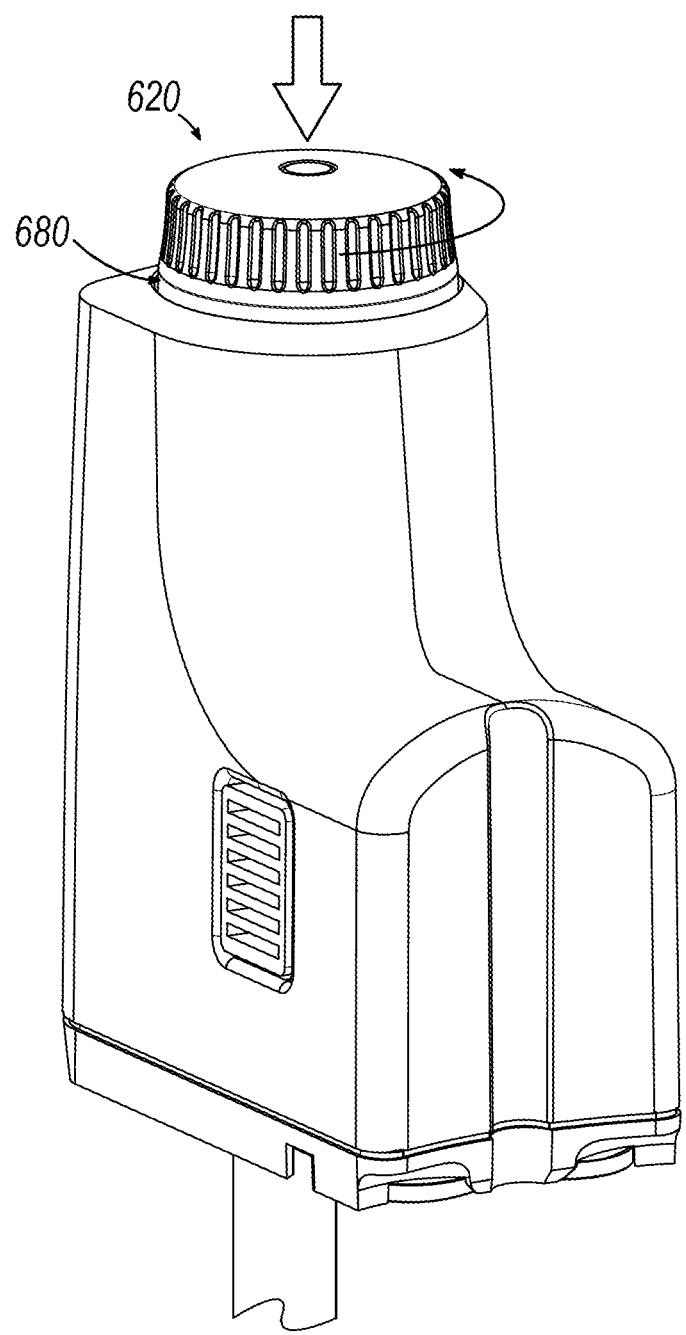
FIG. 22 depicts another perspective view of the manual drive wheel of FIG. 20, with the manual drive wheel in an engaged position.

Unlike manual drive wheels (320, 420) described above, manual drive wheel (620) of the present example includes an instrument retaining feature (680). Instrument retaining feature (680) is generally configured to promote application of force to manual drive wheel (620) along a specific axis to promote engagement between surgical instrument (110) and robotic arm (42) at chassis (122) of surgical instrument (110). As best seen in FIGS. 21 and 22, instrument retaining feature (680) includes a drive lock (682), a resilient feature (684), and a wheel lock (686). Drive lock (682) of the present example defines an irregular configuration similar to a castle nut. As will be described in greater detail below, the configuration of drive lock (682) may be complementary to the configuration of wheel lock (686) to promote releasable engagement between drive lock (682) and wheel lock (686). Although not shown, it should be understood that drive lock (682) may be in communication with other components of bailout mechanisms (310, 410) to transmit rotary motion from manual drive wheel (620) to other drive components of bailout mechanisms (310, 410).

Wheel lock (686) is best seen in FIG. 22. As can be seen, wheel lock (686) extends from an underside surface of manual drive wheel (620). In this configuration, wheel lock (686) is configured to selectively engage drive lock (682) when manual drive wheel (620) is coupled to the rest of surgical instrument (110). The particular configuration of wheel lock (686) is complementary to the particular configuration of drive lock (682). For instance, as noted above, drive lock (682) includes a configuration similar to a castle nut. Thus, wheel lock (686) of the present example likewise includes a configuration similar to a castle nut, but with an opposite pattern to promote mating engagement between drive lock (682) and wheel lock (686).

Although drive lock (682) and wheel lock (686) of the present example use a configuration similar to a castle nut, it should be understood that in other examples various alternative configurations may be used. For instance, the configuration used in the present example provides a paw or cam surface that may be used to selectively transfer rotary motion from wheel lock (686) to drive lock (682). Thus, any other suitable mating surface may be used as will be apparent to those of ordinary skill in the art in view of the teachings herein.

Returning to FIG. 21, resilient feature (684) is disposed between drive lock (682) and wheel lock (686). Resilient feature (684) is generally configured to bias wheel lock (686) away from drive lock (682) such that drive lock (682) and wheel lock (686) may not be matingly engaged unless a suitable force is applied to manual drive wheel (620). Resilient feature (684) of the present example is configured as a coil spring, although in other examples various alternative configurations may be used such as torsion springs, rubber or polymer cylinders, and/or etc.

In use, manual drive wheel (620) may be initially in a disengaged configuration as shown in FIG. 20. In this configuration, resilient feature (684) biases manual drive wheel (620) proximally from surgical instrument (110) such that wheel lock (686) is disengaged from drive lock (682). With wheel lock (686) disengaged from drive lock (682), manual drive wheel (620) may rotate freely without transmitting rotation to any other portion of bailout mechanism (310, 410).

To initiate drive of bailout mechanism (310, 410), a distal force may be applied to manual drive wheel (620) as shown in FIG. 22. This force may overcome the force of resilient feature (684) and drive manual drive wheel (620) distally to engage wheel lock (686) with drive lock (682). Manual drive wheel (620) may then be rotated. During rotation, rotation of manual drive wheel (620) is communicated to other components of bailout mechanism (310, 410) via engagement between wheel lock (686) and drive lock (682).

As manual drive wheel (620) is rotated, distal force sufficient to overcome the resilient bias of resilient feature (684) may be maintained to maintain engagement between wheel lock (686) and drive lock (682). This distal force component may be desirable to force surgical instrument (110) distally toward robotic arm (42) to promote engagement between surgical instrument (110) and robotic arm (42). Without such a distal force component, an operator might apply excessive force to manual drive wheel (620) leading to disengagement of surgical instrument (110) from robotic arm (42). Thus, manual drive wheel (620) of the present example is desirable to prevent inadvertent disengagement between surgical instrument (110) and robotic arm (42).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: a body; a shaft assembly extending distally from the body; an end effector disposed on a distal end of the shaft assembly, wherein the end effector includes a first jaw and a second jaw; an actuation assembly including a pusher member configured to move relative to the end effector to drive movement of the first jaw, the second jaw, or both the first jaw and the second jaw; and a bailout mechanism including a first elongate actuation element and a second elongate actuation element, wherein a portion of the bailout mechanism is configured to selectively apply tension to the first elongate actuation element and the second elongate actuation element to move the pusher member, wherein the first elongate actuation element is stronger in tension than the second elongate actuation element cable.

Example 2

The surgical instrument of Example 1, wherein the bailout mechanism includes a dual capstan configured to receive the first elongate actuation element and the second elongate actuation element with the first actuation cable threaded on the dual capstan opposite of the second actuation cable.

Example 3

The surgical instrument of Examples 1 or 2, wherein the first elongate actuation element defines a first diameter, wherein the second elongate actuation element defines a second diameter, wherein the first diameter is different than the second diameter.

Example 4

The surgical instrument of Examples 1 or 2, wherein the first elongate actuation element defines a first diameter, wherein the second elongate actuation element defines a second diameter, wherein the first diameter is greater than the second diameter.

Example 5

The surgical instrument of any one or more of Examples 1 through 4, wherein the first elongate actuation element is configured to pull the pusher member proximally upon application of tension to the first elongate actuation element.

Example 6

The surgical instrument of any one or more of Examples 1 through 5, wherein the bailout mechanism further includes a shuttle in communication with the pusher member, wherein the first elongate actuation element is configured as a first cable configured to apply tension to the shuttle in a proximal direction, wherein the second elongate actuation element is configured as a second cable configured to apply tension to the shuttle in a distal direction.

Example 7

The surgical instrument of Example 6, further comprising a release feature associated with the shuttle, wherein the release feature is configured to release the second cable from the shuttle upon application of a predetermined force to the second cable.

Example 8

The surgical instrument of Example 7, wherein the release feature comprises a collar crimped or swaged to the second actuation cable.

Example 9

The surgical instrument of Example 7, wherein the release feature comprises a lug disposed within the shuttle and proximate a portion of the second actuation cable.

Example 10

The surgical instrument of any one or more of Examples 1 through 9, wherein the body includes a coupler configured to communicate with a robotic arm, wherein the bailout mechanism further includes a manual drive wheel configured to drive a portion of a bailout mechanism independently of the robotic arm to selectively apply tension to the first elongate actuation element and the second elongate actuation element, wherein the manual drive wheel includes an arm configured to extend from a portion of the manual drive wheel.

Example 11

The surgical instrument of Example 10, wherein the arm is configured to pivot relative to a portion of the manual drive wheel between a retracted configuration to an extended configuration.

Example 12

The surgical instrument of Examples 10 or 11, wherein the manual drive wheel defines a wheel diameter, wherein the arm defines an arm length, wherein the arm length corresponds to the wheel diameter.

Example 13

The surgical instrument of any one or more of Examples 1 through 12, wherein the bailout mechanism further includes a manual drive wheel configured to selectively drive a portion of a bailout mechanism to selectively apply tension to the first elongate actuation element and the second elongate actuation element, wherein the manual drive wheel is configured to move from a drive position to a released position, wherein the manual drive wheel is configured to drive a portion of the bailout mechanism when in the drive position, wherein the manual drive wheel is configured to rotate independently of the bailout mechanism when in the released position.

Example 14

The surgical instrument of Example 13, wherein the manual drive wheel includes a wheel lock configured to engage a drive lock in communication with a portion of the bailout mechanism, wherein the manual drive wheel is resiliently biased to disengage the wheel lock from the drive lock.

Example 15

The surgical instrument of claim 13, wherein the manual drive wheel is configured to move along an actuation axis, wherein the actuation axis is aligned with a longitudinal axis defined by the shaft assembly.

Example 16

A surgical instrument, comprising: a body; a shaft assembly extending distally from the body; an end effector disposed on a distal end of the shaft assembly, wherein the end effector includes a first jaw and a second jaw; an actuation assembly including a pusher member configured to move relative to the end effector to drive movement of the first jaw, the second jaw, or both the first jaw and the second jaw; and a manual drive mechanism including a retraction element and an advancement element, wherein the retraction element is configured to retract the pusher member of the actuation assembly relative to the end effector, wherein the advancement element is configured to advance the pusher member of the actuation assembly relative to the end effector, wherein the retraction element defines a first strength attribute, wherein the advancement element defines a second strength attribute, wherein the first strength attribute is greater than the second strength attribute.

Example 17

The surgical instrument of Example 16, wherein the manual drive mechanism is configured to move the retraction element independently of the advancement element.

Example 18

The surgical instrument of Examples 16 or 17, wherein the first strength attribute corresponds to a first diameter of the retraction element, wherein the second strength attribute corresponds to a second diameter of the advancement element, wherein the first diameter is greater than the second diameter.

Example 19

The surgical instrument of any one or more of Examples 16 through 18, wherein the restriction element is in direct communication with the pusher member of the actuation assembly.

Example 20

A surgical instrument, comprising: a body; a shaft assembly extending distally from the body; an end effector disposed on a distal end of the shaft assembly, wherein the end effector includes a first jaw and a second jaw; an actuation assembly including a pusher member configured to move relative to the end effector to drive movement of the first jaw, the second jaw, or both the first jaw and the second jaw; and a bailout mechanism including a manual drive wheel and a capstan, wherein the capstan is coupled to a first actuation cable and a second actuation cable, wherein the capstan is configured to apply tension to the first actuation cable or the second actuation cable based on the direction of rotation of the capstan, wherein the first actuation cable and the second actuation cable are each in communication with the pusher member such that the first actuation cable and the second actuation cable are each configured to move the pusher member, wherein the first actuation cable defines a first strength attribute, wherein the second actuation cable defines a second strength attribute, wherein the first strength attribute is different than the second strength attribute.

Example 21

A surgical instrument, comprising: a body including a coupler configured to communicate with a robotic arm; a shaft assembly extending distally from the body; an end effector disposed on a distal end of the shaft assembly, wherein the end effector includes a first jaw and a second jaw; an actuation assembly including a pusher member configured to move relative to the end effector to drive movement of the first jaw, the second jaw, or both the first jaw and the second jaw; and a bailout mechanism including a first actuation cable and a second actuation cable, wherein a portion of the bailout mechanism is configured to selectively apply tension to the first actuation cable and the second actuation cable to move the pusher member.

Example 22

The surgical instrument of Example 21, wherein the bailout mechanism further includes a manual drive wheel configured to drive a portion of a bailout mechanism to selectively apply tension to the first actuation cable and the second actuation cable, wherein the manual drive wheel includes an arm configured to extend from a portion of the manual drive wheel.

Example 23

The surgical instrument of Example 22, wherein the arm is configured to pivot relative to a portion of the manual drive wheel between a retracted configuration to an extended configuration.

Example 24

The surgical instrument of Examples 22 or 23, wherein the manual drive wheel defines a wheel diameter, wherein the arm defines an arm length, wherein the arm length corresponds to the wheel diameter.

Example 25

The surgical instrument of any one or more of Examples 21 through 24, wherein the bailout mechanism further includes a manual drive wheel configured to selectively drive a portion of a bailout mechanism to selectively apply tension to the first actuation cable and the second actuation cable, wherein the manual drive wheel is configured to move from a drive position to a released position, wherein the manual drive wheel is configured to drive a portion of the bailout mechanism when in the drive position, wherein the manual drive wheel is configured to rotate independently of the bailout mechanism when in the released position.

Example 26

The surgical instrument of Example 25, wherein the manual drive wheel includes a wheel lock configured to engage a drive lock in communication with a portion of the bailout mechanism, wherein the manual drive wheel is resiliently biased to disengage the wheel lock from the drive lock.

Example 27

The surgical instrument of claim 25, wherein the manual drive wheel is configured to move along an actuation axis, wherein the actuation axis is aligned with a longitudinal axis defined by the shaft assembly.

IV. Miscellaneous

Any one or more of the teachings, expressions, embodiments, examples, etc. described herein may be combined with any one or more of the teachings, expressions, embodiments, examples, etc. described in U.S. patent application Ser. No. 17/402,674, entitled "Methods of Operating a Robotic Surgical Stapler," filed on Aug. 16, 2021, published as U.S. Pub. No. 2023/0051361 on Feb. 16, 2023; U.S. patent application Ser. No. 17/402,675, entitled "Multi-Threshold Motor Control Algorithm for Powered Surgical Stapler," filed on Aug. 16, 2021, published as U.S. Pub. No. 2023/0051271 on Feb. 16, 2023; U.S. patent application Ser. No. 17/402,677, entitled "Variable Response Motor Control Algorithm for Powered Surgical Stapler," filed on Aug. 16, 2021, issued as U.S. Pat. No. 11,944,297 on Apr. 2, 2024; U.S. patent application Ser. No. 17/402,679, entitled "Powered Surgical Stapler Having Independently Operable Closure and Firing Systems," filed on Aug. 16, 2021, issued as U.S. Pat. No. 11,779,332 on Oct. 10, 2023; U.S. patent application Ser. No. 17/402,695, entitled "Firing System Features for Surgical Stapler," filed on Aug. 16, 2021, published as U.S. Pub. No. 2023/0050707 on Feb. 16, 2023; U.S. patent application Ser. No. 17/402,701, entitled "Multiple-Sensor Firing Lockout Mechanism for Powered Surgical Stapler," filed on Aug. 16, 2021, published as U.S. Pub. No. 2023/0050358 on Feb. 16, 2023; U.S. patent application Ser. No. 17/402,703, entitled "Proximally Located Firing Lockout Mechanism for Surgical Stapler," filed on Aug. 16, 2021, issued as U.S. Pat. No. 11,957,336 on Apr. 16, 2024; U.S. patent application Ser. No. 17/402,720, entitled "Cartridge-Based Firing Lockout Mechanism for Surgical Stapler," filed on Aug. 16, 2021, published as U.S. Pub. No. 2023/0051222 on Feb. 16, 2023; U.S. patent application Ser. No. 17/402,732, entitled "Sled Restraining Member for Surgical Stapler," filed on Aug. 16, 2021, published as U.S. Pub. No. 2023/0045893 on Feb. 16, 2023; U.S. patent application Ser. No. 17/402,738, entitled "Firing Member Tracking Feature for Surgical Stapler," filed on Aug. 16, 2021, published as U.S. Pub. No. 2023/0049736 on Feb. 16, 2023; U.S. patent application Ser. No. 17/402,744, entitled "Adjustable Power Transmission Mechanism for Powered Surgical Stapler," filed on Aug. 16, 2021, published as U.S. Pub. No. 2023/0051938 on Feb. 16, 2023; and/or U.S. patent application Ser. No. 17/402,759, entitled "Deflectable Firing Member for Surgical Stapler," filed Aug. 16, 2021, published as U.S. Pub. No. 2023/0052307 on Feb. 16, 2023. The disclosure of each of these applications is incorporated by reference herein in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art.

For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) a body;
   (b) a shaft assembly extending distally from the body;
   (c) an end effector disposed on a distal end of the shaft assembly, wherein the end effector includes a first jaw and a second jaw;
   (d) an actuation assembly including a pusher member configured to move relative to the end effector to drive movement of the first jaw, the second jaw, or both the first jaw and the second jaw; and
   (e) a bailout mechanism including a first elongate actuation element and a second elongate actuation element, wherein a portion of the bailout mechanism is configured to selectively apply tension to the first elongate actuation element and the second elongate actuation element to move the pusher member, wherein the first elongate actuation element is stronger in tension than the second elongate actuation element in tension.

2. The surgical instrument of claim 1, wherein the bailout mechanism includes a dual capstan configured to receive the first elongate actuation element and the second elongate actuation element with the first actuation element threaded on the dual capstan opposite of the second actuation element.

3. The surgical instrument of claim 1, wherein the first elongate actuation element defines a first diameter, wherein the second elongate actuation element defines a second diameter, wherein the first diameter is different than the second diameter.

4. The surgical instrument of claim 1, wherein the first elongate actuation element defines a first diameter, wherein the second elongate actuation element defines a second diameter, wherein the first diameter is greater than the second diameter.

5. The surgical instrument of claim 4, wherein the first elongate actuation element is configured to pull the pusher member proximally upon application of tension to the first elongate actuation element.

6. The surgical instrument of claim 1, wherein the bailout mechanism further includes a shuttle in communication with the pusher member, wherein the first elongate actuation element is configured as a first cable configured to apply tension to the shuttle in a proximal direction, wherein the second elongate actuation element is configured as a second cable configured to apply tension to the shuttle in a distal direction.

7. The surgical instrument of claim 6, further comprising a release feature associated with the shuttle, wherein the release feature is configured to release the second cable from the shuttle upon application of a predetermined force to the second cable.

8. The surgical instrument of claim 7, wherein the release feature comprises a collar crimped or swaged to the second actuation cable.

9. The surgical instrument of claim 7, wherein the release feature is disposed within the shuttle and proximate a portion of the second cable.

10. The surgical instrument of claim 1, wherein the body includes a coupler configured to communicate with a robotic arm, wherein the bailout mechanism further includes a manual drive wheel configured to drive a portion of a bailout mechanism independently of the robotic arm to selectively apply tension to the first elongate actuation element and the second elongate actuation element, wherein the manual drive wheel includes an arm configured to extend from a portion of the manual drive wheel.

11. The surgical instrument of claim 10, wherein the arm is configured to pivot relative to a portion of the manual drive wheel between a retracted configuration to an extended configuration.

12. The surgical instrument of claim 10, wherein the manual drive wheel defines a wheel diameter, wherein the arm defines an arm length, wherein the arm length corresponds to the wheel diameter.

13. The surgical instrument of claim 1, wherein the bailout mechanism further includes a manual drive wheel configured to selectively drive a portion of a bailout mechanism to selectively apply tension to the first elongate actuation element and the second elongate actuation element, wherein the manual drive wheel is configured to move from a drive position to a released position, wherein the manual drive wheel is configured to drive a portion of the bailout mechanism when in the drive position, wherein the manual drive wheel is configured to rotate independently of the bailout mechanism when in the released position.

14. The surgical instrument of claim 13, wherein the manual drive wheel includes a wheel lock configured to engage a drive lock in communication with a portion of the bailout mechanism, wherein the manual drive wheel is resiliently biased to disengage the wheel lock from the drive lock.

15. The surgical instrument of claim 13, wherein the manual drive wheel is configured to move along an actuation axis, wherein the actuation axis is aligned with a longitudinal axis defined by the shaft assembly.

16. A surgical instrument, comprising:
(a) a body;
(b) a shaft assembly extending distally from the body;
(c) an end effector disposed on a distal end of the shaft assembly, wherein the end effector includes a first jaw and a second jaw;
(d) an actuation assembly including a pusher member configured to move relative to the end effector to drive movement of the first jaw, the second jaw, or both the first jaw and the second jaw; and
(e) a manual drive mechanism including a retraction element and an advancement element, wherein the retraction element is configured to retract the pusher member of the actuation assembly relative to the end effector, wherein the advancement element is configured to advance the pusher member of the actuation assembly relative to the end effector, wherein the retraction element defines a first tensile strength attribute, wherein the advancement element defines a second tensile strength attribute, wherein the first tensile strength attribute is greater than the second tensile strength attribute.

17. The surgical instrument of claim 16, wherein the manual drive mechanism is configured to move the retraction element independently of the advancement element.

18. The surgical instrument of claim 16, wherein the first tensile strength attribute corresponds to a first diameter of the retraction element, wherein the second tensile strength attribute corresponds to a second diameter of the advancement element, wherein the first diameter is greater than the second diameter.

19. The surgical instrument of claim 17, wherein the retraction element is in direct communication with the pusher member of the actuation assembly.

20. A surgical instrument, comprising:
(a) a body;
(b) a shaft assembly extending distally from the body;
(c) an end effector disposed on a distal end of the shaft assembly, wherein the end effector includes a first jaw and a second jaw;
(d) an actuation assembly including a pusher member configured to move relative to the end effector to drive movement of the first jaw, the second jaw, or both the first jaw and the second jaw; and
(e) a bailout mechanism including a manual drive wheel and a capstan, wherein the capstan is coupled to a first actuation cable and a second actuation cable, wherein the capstan is configured to apply tension to the first actuation cable or the second actuation cable based on the direction of rotation of the capstan, wherein the first actuation cable and the second actuation cable are each in communication with the pusher member such that the first actuation cable and the second actuation cable are each configured to move the pusher member, wherein the first actuation cable defines a first axial strength attribute, wherein the second actuation cable defines a second axial strength attribute, wherein the first axial strength attribute is different than the second axial strength attribute.

* * * * *